United States Patent
Adachi et al.

(10) Patent No.: US 9,149,214 B2
(45) Date of Patent: Oct. 6, 2015

(54) ANNOYANCE JUDGMENT SYSTEM, APPARATUS, METHOD, AND PROGRAM

(71) Applicant: Panasonic Corporation, Osaka (JP)

(72) Inventors: Shinobu Adachi, Nara (JP); Jun Ozawa, Nara (JP); Koji Morikawa, Kyoto (JP); Yumiko Kato, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 465 days.

(21) Appl. No.: 13/630,113

(22) Filed: Sep. 28, 2012

(65) Prior Publication Data

US 2013/0039498 A1 Feb. 14, 2013

Related U.S. Application Data

(63) Continuation of application No. PCT/JP2011/006435, filed on Nov. 18, 2011.

(30) Foreign Application Priority Data

Nov. 24, 2010 (JP) .................................. 2010-261372
Nov. 24, 2010 (JP) .................................. 2010-261373

(51) Int. Cl.
*A61B 5/04* (2006.01)
*H04R 29/00* (2006.01)
(Continued)

(52) U.S. Cl.
CPC .............. *A61B 5/12* (2013.01); *A61B 5/04845* (2013.01); *H04R 25/70* (2013.01); *H04R 2225/43* (2013.01)

(58) Field of Classification Search
USPC ....................................... 600/544; 381/58, 60
See application file for complete search history.

(56) References Cited

U.S. PATENT DOCUMENTS 6,602,202 B2 * 8/2003 John et al. ..................... 600/559
2008/0037797 A1 2/2008 Goldstein et al.
(Continued)

FOREIGN PATENT DOCUMENTS

CN 101770779 7/2007
JP 60-219000 A 11/1985
(Continued)

OTHER PUBLICATIONS

International Search Report for corresponding International Application No. PCT/JP2011/006435 mailed Jan. 31, 2012.
(Continued)

*Primary Examiner* — Etsub Berhanu
(74) *Attorney, Agent, or Firm* — Renner, Otto, Boisselle & Sklar, LLP

(57) ABSTRACT

An annoyance judgment system includes: a biological signal measurement section configured to measure an electroencephalogram signal of a user; a database retaining a plurality of monosyllabic speech sounds such that, for each speech sound, the speech sound and a reference latency of an electroencephalogram negative component corresponding to the speech sound are retained in association; a presented-speech sound determination section configured to determine a monosyllabic speech sound to be presented by referring to the database; and an annoyance judgment section configured to judge annoyance of the output speech sound by comparing a peak latency of a negative component of the electroencephalogram signal in a range from 50 ms to 350 ms from a starting point, the a starting point being a point in time at which the determined speech sound is presented, against the reference latency corresponding to the determined speech sound that is retained in the database.

20 Claims, 25 Drawing Sheets

(51) Int. Cl.
  *A61B 5/12* (2006.01)
  *A61B 5/0484* (2006.01)
  *H04R 25/00* (2006.01)

(56) References Cited

U.S. PATENT DOCUMENTS

2009/0259277 A1* 10/2009 Cornejo Cruz et al. ......... 607/57
2010/0067710 A1   3/2010 Hendriks et al.
2011/0071828 A1   3/2011 Adachi et al.

FOREIGN PATENT DOCUMENTS

| JP | 06-114038 A | 4/1994 |
| JP | 08-275297 A | 10/1996 |
| JP | 09-038069 A | 2/1997 |
| JP | 09038069 A * | 2/1997 |
| WO | 2010/073614 A1 | 7/2010 |

OTHER PUBLICATIONS

Tamesue et al., "Kioku Seishin Sagyoji no Soon ni Taisuru Shinri-Seiriteki Teiryo Hyoka ni Kansuru Kisoteki Kosatsu (or A Basic Discussion of Psychological/Physiologcial Quantitative Evaluations with respect to Noises at Memorization Mental Tasks)", Report of the 2009 Spring Meeting, the Acoustical Society of Japan Koen Yoshi-Koen Ronbun CD-ROM, Mar. 10, 2009, pp. 1031-1032 and concise explanation.

Shinya Kuriki, "Measurements of Auditory Evoked Neuromagnetic Field Using a Multichannel SQUID Magnetometer", Journal of the Acoustical Society of Japan, May 1992, vol. 48, No. 5, pp. 320-327 and concise explanation.

Hosoi et al., "Hochouki Tekigokensa no Shinshin 2008 (or 2008 Guidelines for Hearing Aid Suitability Test)", 2008 and concise explanation (cited in [0009] of the specification).

Kazuoki Kodera, "Hochoki Fittingu No Kangaekata (or Concept of Hearing Aid Fitting)", Shindan to Chiryosha, 1999, p. 166 and concise explanation (cited in [0012] of the specification).

"Jishoukanrendeni (ERP) Manyuaru-P300 WO Chushinni (or Event-Related Potential (ERP) Manual-mainly concerning P300)", edited by Kimitaka Kaga et al., Shinohara Shuppan Shinsha, 1995, p. 30 and partial English translation (cited in [0122] of the specification).

Chinese Search Report (with English translation) for corresponding Chinese Patent Application No. 201180037851.8 dated Jun. 25, 2015.

* cited by examiner

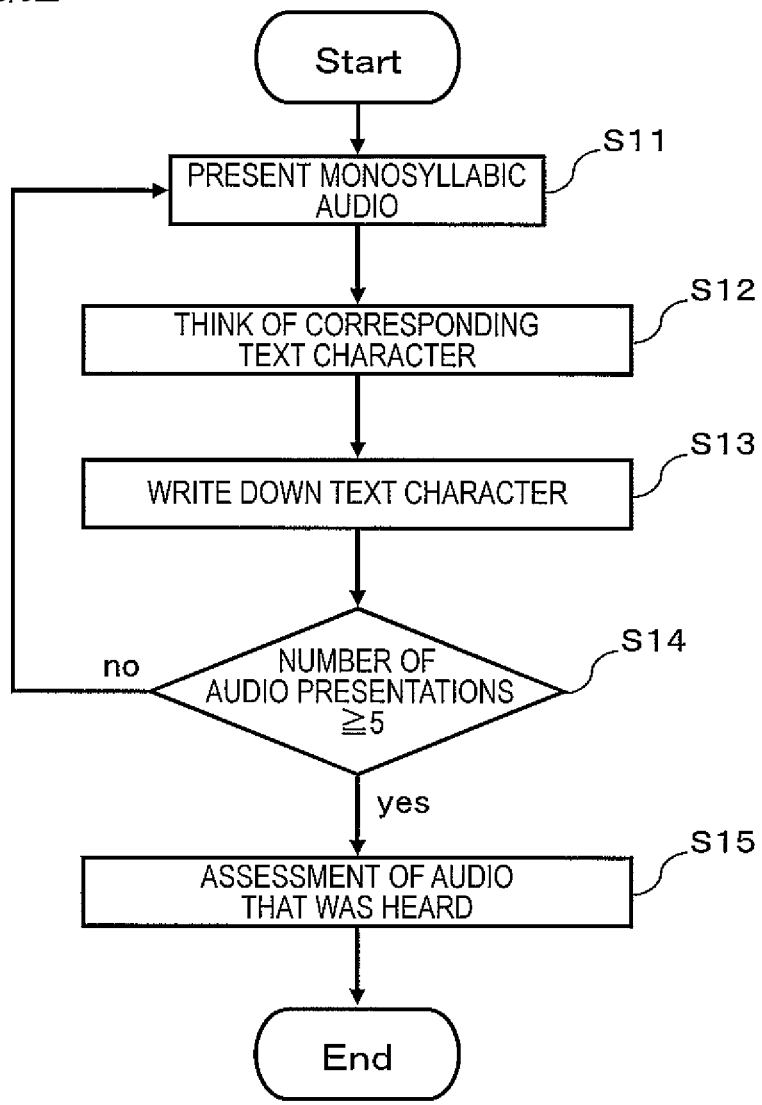

|  |  | FLAT/DISTORTED ||
|  |  | FLAT | DISTORTED |
| --- | --- | --- | --- |
| SOUND PRESSURE | LARGE | LF CONDITION 75−85dB | LD CONDITION 75−85dB |
|  | MIDDLE | MF CONDITION 60−65dB | MD CONDITION 60−65dB |
|  | SMALL | SF CONDITION 40−45dB | SD CONDITION 40−45dB |

*FIG.4A*
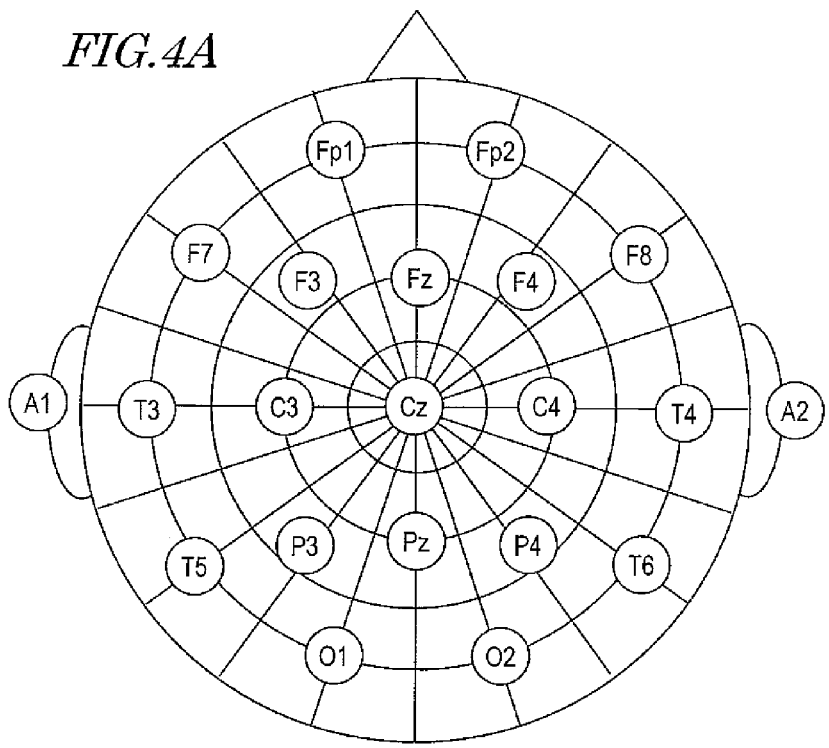
*FIG.4B*
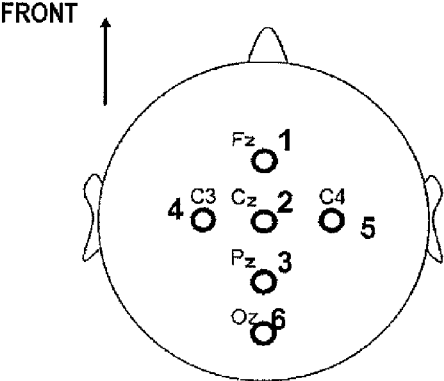
<UPPER VIEW>
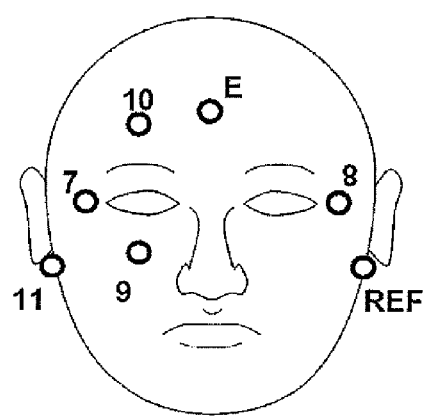
<FRONT VIEW>

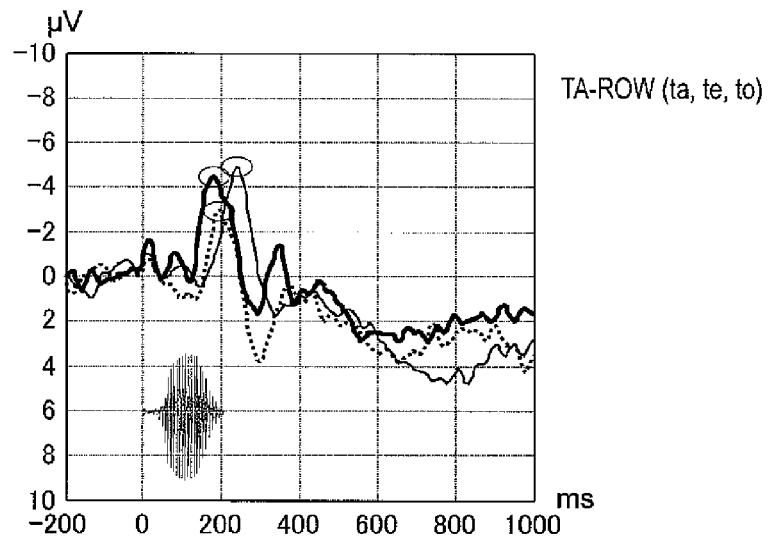
FIG.8A  TA-ROW (ta, te, to)
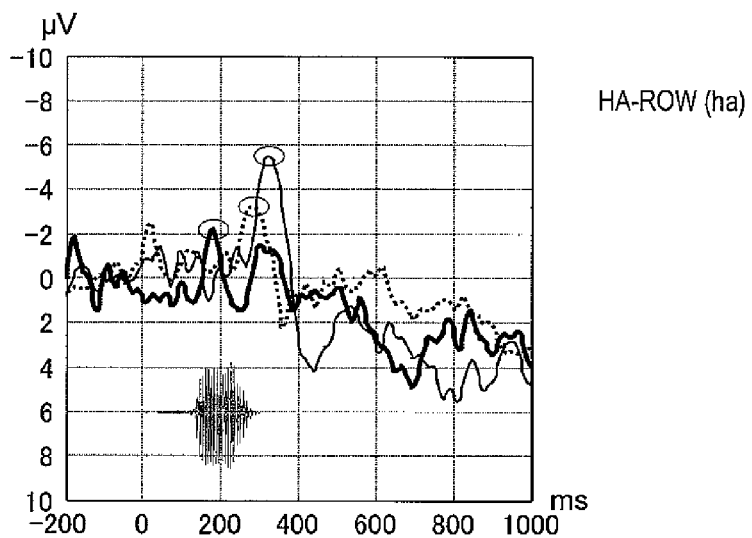
FIG.8B  HA-ROW (ha)
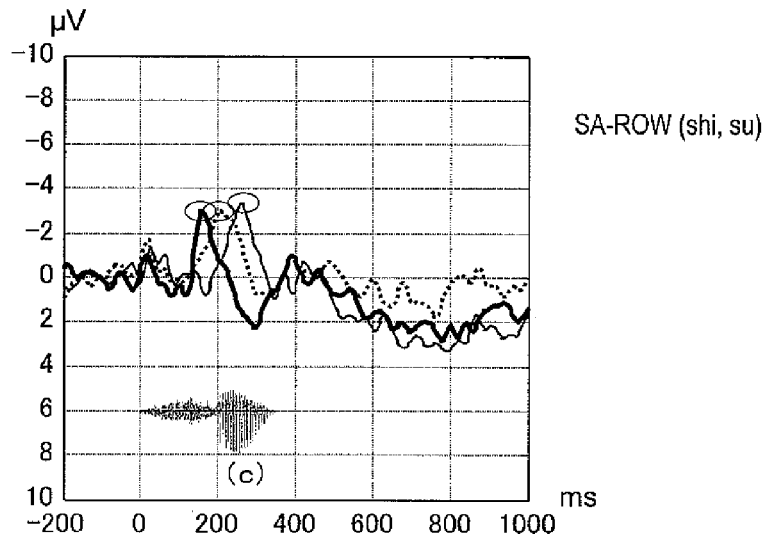
FIG.8C  SA-ROW (shi, su)

| | A | B |
|---|---|---|
| RESULT OF LATENCY COMPARISON | N1 COMPONENT LATENCY IS SHORTER THAN PREDETERMINED THRESHOLD VALUE | N1 COMPONENT LATENCY IS LONGER THAN PREDETERMINED THRESHOLD VALUE |
| RESULT OF ANNOYANCE JUDGMENT | ANNOYING | NOT ANNOYING |

| SPEECH SOUND | AUDIO FILE | CONSONANT LABEL | REFERENCE N1 COMPONENT LATENCY |
|---|---|---|---|
| a | a.wav | – | 130 |
| u | u.wav | – | 130 |
| o | o.wav | – | 130 |
| shi | shi.wav | s | 160 |
| su | su.wav | s | 160 |
| ki | ki.wav | k | 180 |
| ku | ku.wav | k | 180 |
| ta | ta.wav | t | 175 |
| te | te.wav | t | 175 |
| to | to.wav | t | 175 |
| ha | ha.wav | h | 190 |
| yo | yo.wav | y | 150 |
| ri | ri.wav | r | 180 |
| wa | wa.wav | w | 150 |
| ni | ni.wav | n | 155 |
| ne | ne.wav | n | 155 |
| mo | mo.wav | m | 150 |
| ga | ga.wav | g | 140 |
| ji | ji.wav | j | 180 |
| ba | ba.wav | b | 150 |

71

ANNOYANCE

| SPEECH SOUND | 55dB | 65dB | 75dB | 85dB |
|---|---|---|---|---|
| a | 0 | 0 | 1 | 1 |
| u | 0 | 0 | 0 | 1 |
| o | 0 | 0 | 0 | 1 |
| shi | 0 | 0 | 1 | 1 |
| su | 0 | 1 | 1 | 1 |
| ki | 0 | 0 | 0 | 0 |
| ku | 0 | 0 | 0 | 0 |
| ta | 1 | 1 | 1 | 1 |
| te | 0 | 1 | 1 | 1 |
| to | 0 | 0 | 1 | 1 |
| ha | 1 | 0 | 1 | 1 |
| yo | 0 | 0 | 0 | 0 |
| ri | 0 | 0 | 0 | 0 |
| wa | 0 | 0 | 1 | 1 |
| ni | 0 | 0 | 0 | 1 |
| ne | 0 | 1 | 1 | 1 |
| mo | 0 | 0 | 1 | 1 |
| ga | 0 | 0 | 0 | 0 |
| ji | 0 | 0 | 0 | 1 |
| ba | 0 | 0 | 0 | 0 |

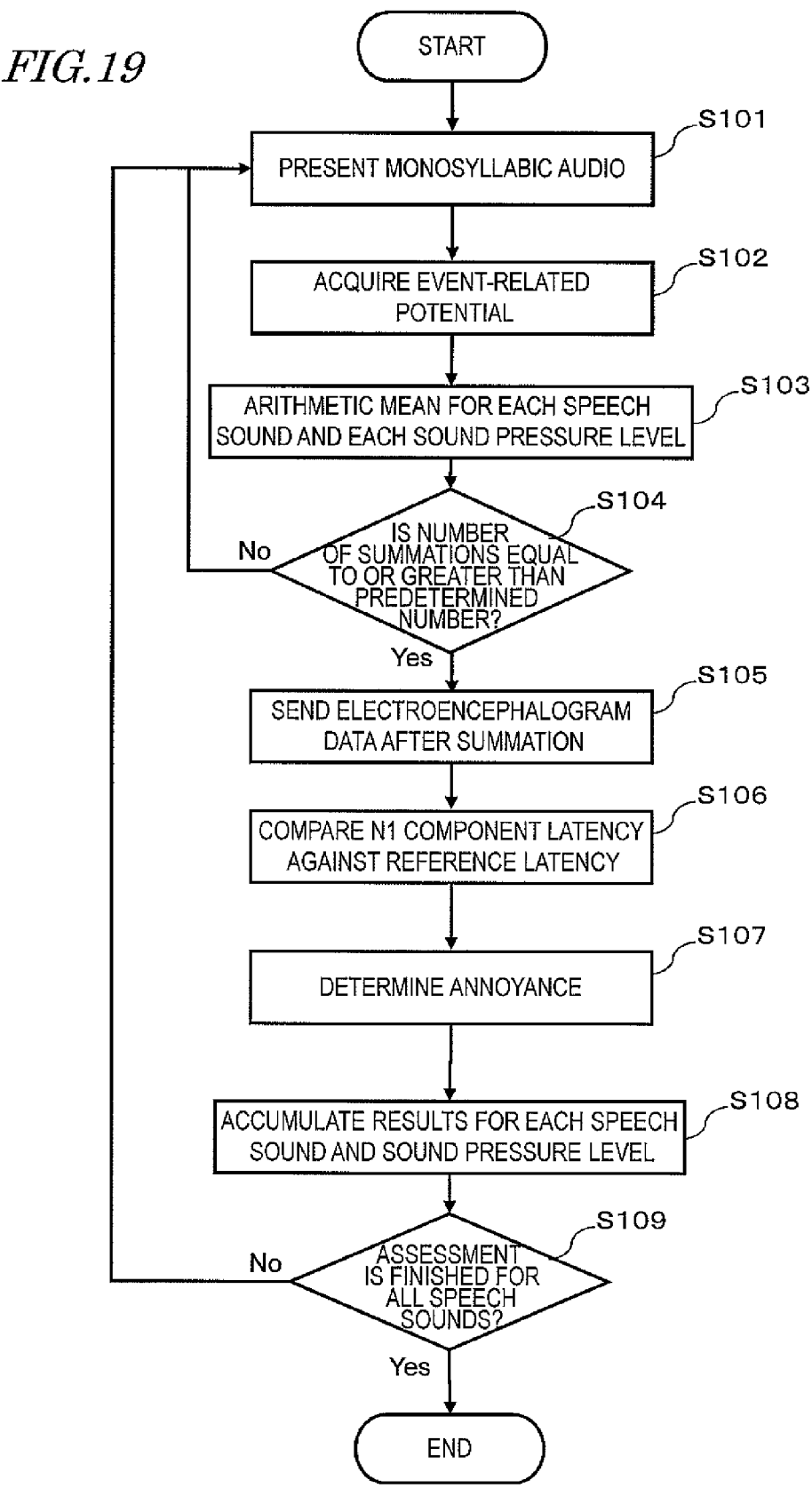

FIG.20

| WORD | 55dB | 65dB | 75dB | 85dB |
|---|---|---|---|---|
| sit | 0 | 0 | 1 | 1 |
| meet | 0 | 0 | 0 | 1 |
| get | 0 | 0 | 0 | 1 |
| cat | 0 | 0 | 1 | 1 |
| come | 0 | 1 | 1 | 1 |
| hot | 0 | 0 | 0 | 0 |
| law | 0 | 0 | 0 | 0 |
| book | 1 | 1 | 1 | 1 |
| blue | 0 | 1 | 1 | 1 |
| urge | 0 | 0 | 1 | 1 |
| star | 1 | 0 | 1 | 1 |
| page | 0 | 0 | 0 | 0 |
| sky | 0 | 0 | 0 | 0 |
| join | 0 | 0 | 1 | 1 |
| now | 0 | 0 | 0 | 1 |
| home | 0 | 1 | 1 | 1 |
| here | 0 | 0 | 1 | 1 |
| care | 0 | 0 | 0 | 0 |
| ... | ... | ... | ... | ... |

FIG.22

ACOUSTIC AIDING PROCESS A

| SPEECH SOUND | 55dB | 65dB | 75dB | 85dB |
|---|---|---|---|---|
| a | 0 | 0 | 1 | 1 |
| u | 0 | 0 | 0 | 1 |
| o | 0 | 0 | 0 | 1 |
| shi | 0 | 0 | 1 | 1 |
| su | 0 | 1 | 1 | 1 |
| ki | 0 | 0 | 0 | 0 |
| ku | 0 | 0 | 0 | 0 |
| ta | 1 | 1 | 1 | 1 |
| te | 0 | 1 | 1 | 1 |
| to | 0 | 0 | 1 | 1 |
| ha | 1 | 0 | 1 | 1 |
| yo | 0 | 0 | 0 | 0 |
| ri | 0 | 0 | 0 | 0 |
| wa | 0 | 0 | 1 | 1 |
| ni | 0 | 0 | 0 | 1 |
| ne | 0 | 1 | 1 | 1 |
| mo | 0 | 0 | 1 | 1 |
| ga | 0 | 0 | 0 | 0 |
| ji | 0 | 0 | 0 | 1 |
| ba | 0 | 0 | 0 | 0 |

(a)

ACOUSTIC AIDING PROCESS B

| SPEECH SOUND | 55dB | 65dB | 75dB | 85dB |
|---|---|---|---|---|
| a | 0 | 0 | 1 | 1 |
| u | 0 | 0 | 0 | 1 |
| o | 0 | 0 | 0 | 1 |
| shi | 0 | 0 | 1 | 1 |
| su | 0 | 1 | 1 | 1 |
| ki | 0 | 0 | 0 | 0 |
| ku | 0 | 0 | 1 | 1 |
| ta | 0 | 0 | 1 | 1 |
| te | 0 | 1 | 1 | 1 |
| to | 0 | 0 | 0 | 1 |
| ha | 1 | 0 | 1 | 1 |
| yo | 0 | 0 | 0 | 0 |
| ri | 0 | 0 | 0 | 0 |
| wa | 0 | 0 | 1 | 1 |
| ni | 0 | 0 | 0 | 1 |
| ne | 0 | 0 | 0 | 1 |
| mo | 0 | 0 | 1 | 1 |
| ga | 0 | 0 | 0 | 0 |
| ji | 0 | 0 | 0 | 1 |
| ba | 0 | 0 | 0 | 0 |

(b)

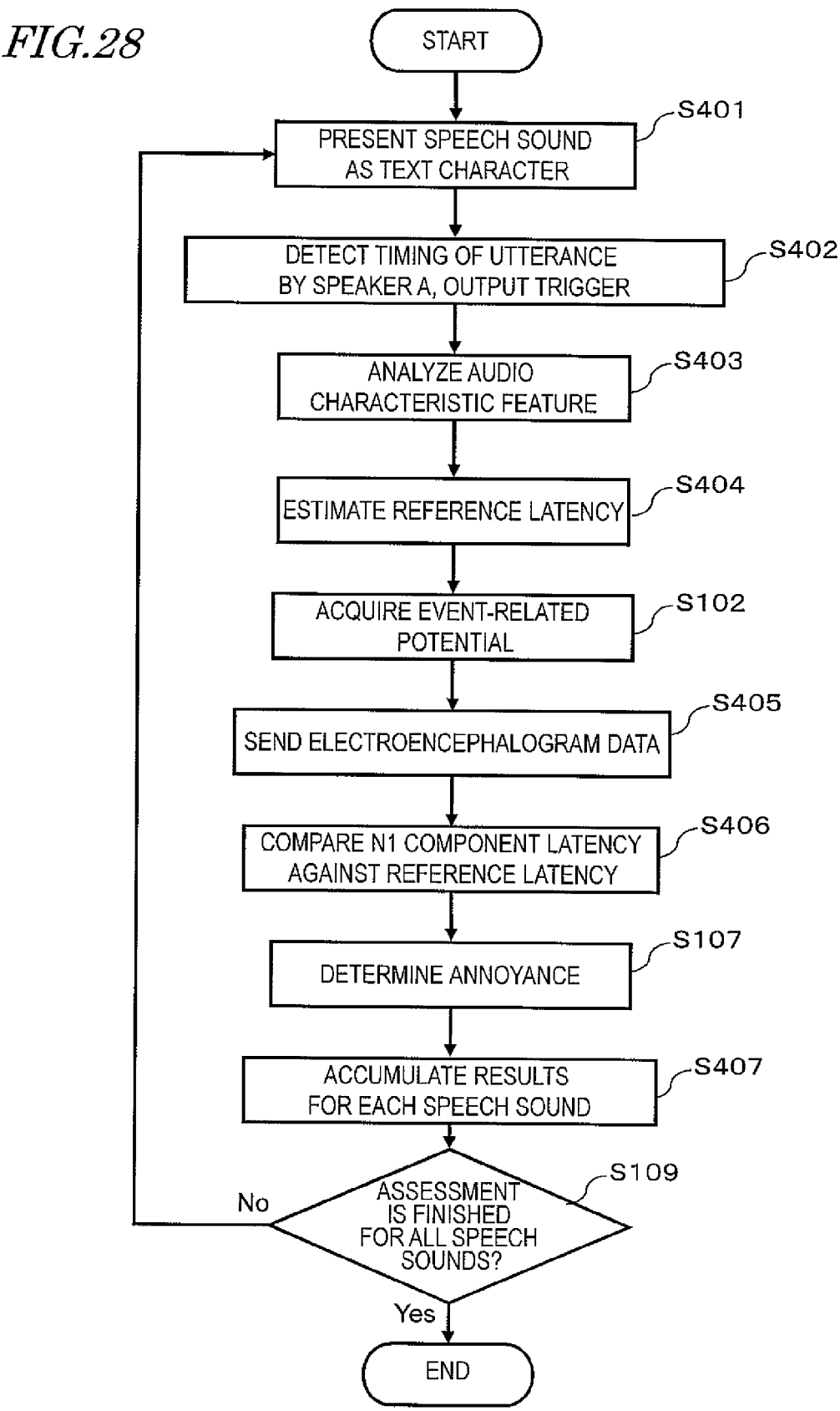

ANNOYANCE JUDGMENT SYSTEM, APPARATUS, METHOD, AND PROGRAM

This is a continuation of International Application No. PCT/JP2011/006435, with an international filing date of Nov. 18, 2011, which claims priority of Japanese Patent Application Nos. 2010-261372, and 2010-261373, both filed on Nov. 24, 2010, the contents of which are hereby incorporated by reference.

BACKGROUND

1. Technical Field

The present application relates to a technique of assessing (judging) whether a user has been able to comfortably listen to a speech sound or not.

2. Description of the Related Art

In recent years, people suffering from hypacusia caused by aging are increasing in number due to the aging society. Due to increased opportunities for listening to loud music for long hours as well as other influences, there is an increasing number of young people suffering from hypacusia. Moreover, due to the downsizing and improved performance of hearing aids, users have come to wear hearing aids without a psychological barrier. Against this background, there is an increasing number of users who wear hearing aids in order to improve their conversational aural distinction abilities.

A hearing aid compensates for the deteriorated hearing of a user by increasing the amplitude of signals of specific frequencies, among various frequencies that compose sounds that are difficult for the user to hear. A hearing aid is required to adjust the amount by which it amplifies sounds, in accordance with the level of deterioration in the hearing of the user. Therefore, before beginning use of a hearing aid, "fitting" is required for adjusting the amount of sound amplification in accordance with the hearing of each user.

Fitting means keeping the output sound pressure (i.e. fluctuations in air pressure that are perceivable as a sound) of each sound frequency at an MCL (most comfortable level: a sound pressure that is felt comfortable to a user). Thus, appropriate fitting is yet to be attained under (1) an insufficient amount of amplification, or (2) an excessive amount of amplification. For example, under an insufficient amount of amplification, the user cannot aurally distinguish audios, thus falling short of the purpose of wearing a hearing aid. Under an excessive amount of amplification, the user is capable of audio distinction; however, there is a problem in that the user may feel annoyed by the audios, which prevents them from using the hearing aid over a long time. Therefore, a fitting needs to be done in such a manner that neither (1) nor (2) occurs. Especially in the case of (2), sounds which are louder than necessary will be presented from the hearing aid, thus possibly hurting the ears of the user.

A first step of fitting is measuring an audiogram. An "audiogram" refers to a measurement of a smallest sound pressure of a pure tone that allows it to be heard; for example, a diagram in which, for each of a number of sounds of different frequencies, the smallest sound pressure (decibel value) that the user can aurally comprehend is plotted against frequency (e.g., 250 Hz, 500 Hz, 1000 Hz, 2000 Hz, 4000 Hz).

Next, based on a fitting theory, which is a mathematical function for estimating an amount of amplification for each frequency, an amount of amplification for each frequency is determined from the resultant audiogram.

However, from an audiogram/fitting theory-based adjustment alone, one cannot know whether an optimum fitting has been realized for improving the intelligibility in aural distinction of conversations. Possible reasons are, for example: an audiogram is not in one-to-one correspondence with a conversational aural distinction ability; a person suffering from hypacusia has a narrow range of sound pressure that is felt to him or her as an appropriate loudness, which makes adjustment difficult; and so on.

Therefore, upon wearing a hearing aid which has been determined and adjusted by the aforementioned method, a hearing aid suitability test is to be carried out (see, for example, Hiroshi HOSOI et al., HOCHOUKI TEKIGO-KENSA NO SHISHIN 2008, or "2008 Guidelines For Hearing Aid Suitability Test", 2008). There are two mandatory test items in a hearing aid suitability test: (1) measurement of a speech sound intelligibility curve, and (2) measurement of an ambient noise tolerance level.

In the measurement of a speech sound intelligibility curve, both when wearing a hearing aid and when not wearing a hearing aid (naked ear), monosyllabic speech sounds are presented at 55 dB SPL (Sound pressure level), 65 dB SPL, 75 dB SPL, and 85 dB SPL; and the speech sound intelligibility at each sound pressure is plotted for comparison. Then, if the intelligibility appears improved when wearing a hearing aid relative to when not wearing a hearing aid, it is determined as suitable.

As used herein, "speech sound intelligibility" refers to an index as to how well a monosyllabic speech sound has been aurally comprehended. A speech sound intelligibility reflects a level of aural distinction during conversations. A "monosyllabic speech sound" means either a single vowel or a combination of a consonant and a vowel (e.g., "あ (a)"/"だ (da)"/"し (shi)").

Speech sound intelligibility is assessed through the following procedure (see, for example, Kazuoki KODERA, "HOCHOKI FITTINGU NO KANGAEKATA (or "Concept of Hearing Aid Fitting"), Shindan To Chiryosha, 1999, p. 166). First, audios in the 67S list (20 speech sounds) proposed by the Japan Audiological Society are reproduced one by one, which a user is allowed to hear. Next, through oral explanation, writing, or other methods, the user is asked to answer which speech sound he or she has aurally comprehended the presented speech sound to be. Then, an evaluator matches the answers against the speech sounds which have been presented, and calculates a correctness rate, which is a rate of speech sounds that have been correctly aurally comprehended among the total of 20 speech sounds. This correctness rate is the speech sound intelligibility.

Various techniques have been disclosed in the past concerning methods of speech sound intelligibility assessment. For example, Japanese Laid-Open Patent Publication No. 9-038069 discloses a speech sound intelligibility assessment method which employs a personal computer (PC) to automatically perform correctness determination. This publication proposes a method in which monosyllabic audios are presented to a user by using a PC; the user is asked to answer with a mouse or by touching a pen to the display; the answers are received as inputs to the PC; and correctness determinations as to the presented audios and answer inputs are automatically made. Since answer inputs are received with a mouse or a pen touch, there is no need for the evaluator to distinguish and analyze the user's answers (which are given by oral explanation or writing), whereby the trouble of the evaluator is reduced.

Moreover, for example, Japanese Laid-Open Patent Publication No. 6-114038 discloses a speech sound intelligibility assessment method in which, after audio presentation, possible choices of speech sounds are presented in the form of text characters. In this publication, choices are limited to only a small number so that the relevant speech sound can be found among the small number of characters, whereby the user's trouble of finding the character is reduced.

On the other hand, in the measurement of an ambient noise tolerance level, sounds which are read aloud are simultaneously presented with ambient noise, and after the sounds which are read aloud are heard, an assessment is made as to whether the ambient noise is tolerable or not (KODERA, et al., supra). Specifically, sounds which are read aloud are presented at 65 dB SPL, and ambient noise is presented at 55 dB SPL, and a subjective impression as to whether the ambient noise is tolerable or not is to be reported. As the subjective impression, it is to be reported whether one can endure using a hearing aid when listening to sounds which are read aloud in the presence of noise, or it is difficult to wear a hearing aid in the presence of noise. The former case is determined as suitable, whereas the latter case is determined as unsuitable.

SUMMARY

The prior art technique needs further improvement in view of assesment of a user state concerning annoyance in speech sound listening.

One non-limiting and exemplary embodiment disclosed herein is directed to provide a way to assess a user state concerning annoyance in speech sound listening.

An annoyance judgment system according to an embodiment disclosed herein comprises: a biological signal measurement section for measuring an electroencephalogram signal of a user; a speech sound database retaining a plurality of monosyllabic speech sounds such that, for each speech sound, the speech sound and a reference latency of an electroencephalogram negative component corresponding to the speech sound are retained in association; a presented-speech sound determination section configured to determine a monosyllabic speech sound to be presented by referring to the speech sound database; an output section configured to present the determined speech sound to the user; and an annoyance judgment section configured to judge annoyance of the output speech sound by comparing a peak latency of a negative component of the electroencephalogram signal in a range from 50 ms to 350 ms from a starting point, the starting point being a point in time at which the speech sound is presented, against the reference latency corresponding to the determined speech sound that is retained in the speech sound database.

According to the present disclosure, there is provided a way to assess a user state concerning annoyance in speech sound listening.

These general and specific aspects may be implemented using a system, a method, and a computer program, and any combination of systems, methods, and computer programs.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

BRIEF DESCRIPTION OF THE DRAWINGS

FIG. 2 is a flowchart showing a procedure corresponding to one trial.

FIG. 4A is a diagram showing electrode positions according to the International 10-20 system, and FIG. 4B is a diagram showing electrode positioning for wearing an electroencephalograph.

FIGS. 8A to 8C show exemplary arithmetic mean waveforms for each group of speech sounds sharing the same consonant.

FIG. 19 is a flowchart showing a procedure of processing which is performed in the annoyance judgment system 100 for speech sound listening.

FIG. 20 is a diagram showing an exemplary assessment result for different monosyllabic words.

FIG. 22 is diagrams showing examples of accumulated results of annoyance judgment using a technique of Embodiment 2.

FIG. 28 is a flowchart showing a processing procedure of the annoyance judgment system 400 for speech sound listening according to Embodiment 4.

DETAILED DESCRIPTION

Figure 1:
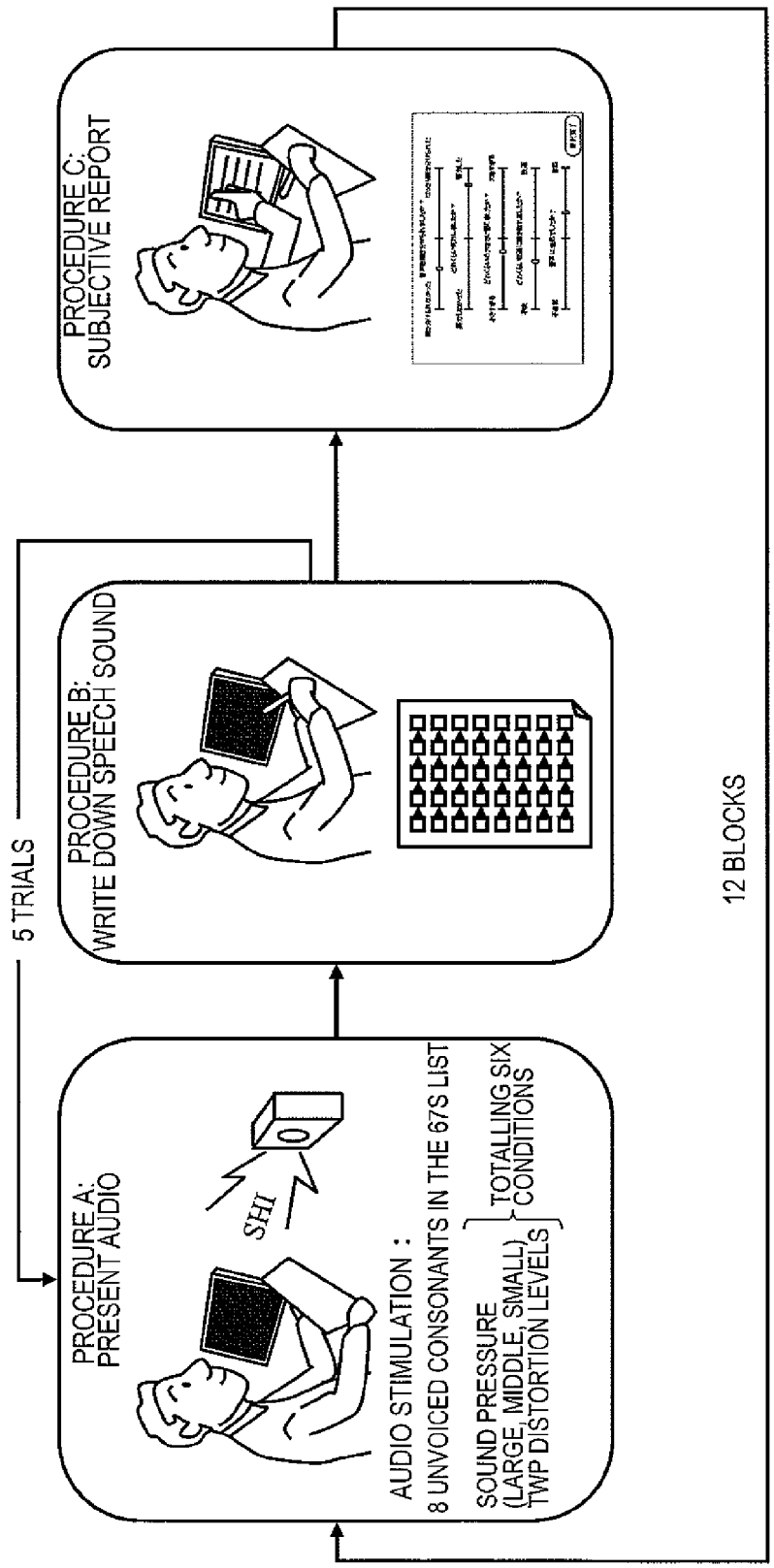
FIG. 1 is a diagram showing the experimental procedure of an electroencephalogram measurement experiment in outline.

In the speech sound intelligibility curve measurement of the aforementioned hearing aid suitability test, a suitable state is determined based only on speech sound intelligibility, while giving no consideration as to whether the user felt annoyed when listening to the speech sound. Therefore, even if annoyance is felt when listening to the speech sound, if the intelligibility which is obtained when wearing a hearing aid is higher than that obtained when not wearing a hearing aid, the acoustic aiding process is assessed as suitable. On the other hand, in the measurement of an ambient noise tolerance level, an assessment is made as to whether the ambient noise is tolerable, while making no assessment as to the annoyance in speech sound listening. In these assessments, even an acoustic aiding process that allows the user to feel annoyed in speech sound listening, such that hearing fatigue is likely to occur, may have been determined as suitable. Annoyance in speech sound listening is a burden on a user who wears a hearing aid on a daily basis.

An annoyance judgment system according to an embodiment disclosed herein comprises: a biological signal measurement section for measuring an electroencephalogram signal of user; a speech sound database retaining a plurality of monosyllabic speech sounds such that, for each speech sound, the speech sound and a reference latency of an electroencephalogram negative component corresponding to the speech sound are retained in association; a presented-speech sound determination section configured to determine a monosyllabic speech sound to be presented by referring to the speech sound database; an output section configured to present the determined speech sound to the user; and an annoyance judgment section configured to judge annoyance of the output speech sound by comparing a peak latency of a negative component of the electroencephalogram signal in a range from 50 ms to 350 ms from a starting point, the starting point being a point in time at which the speech sound is presented, against the reference latency corresponding to the determined speech sound that is retained in the speech sound database.

The speech sound database may keep the association between each speech sound and a reference latency of an electroencephalogram negative component corresponding to the speech sound on the basis of a duration or intensity of a consonant contained in the speech sound.

If the peak latency of the negative component is equal to or smaller than the reference latency, the annoyance judgment section may judge that the audio signal is annoying to the user, and if the peak latency of the negative component is greater than the reference latency, the annoyance judgment section may judge that the audio signal is not annoying to the user.

The annoyance judgment system may further comprise an event-related potential processing section configured to take a summation of event-related potentials of the electroencephalogram signal according to a predetermined criterion and configured to output a result of summation to the annoyance judgment section, wherein, the presented-speech sound determination section may determine two or more speech sounds; the output section sequentially may present the determined speech sounds; and among the determined speech sounds, the event-related potential processing section may take a summation of event-related potentials for speech sounds of a same speech sound type or a same sound pressure, each event-related potential being based on a point in time of presenting the respective speech sound as a starting point.

As the peak latency, the annoyance judgment section may adopt: a point in time at which a negative component of the electroencephalogram signal in a range from 50 ms to 350 ms from a starting point takes a smallest potential, the starting point being a point in time at which the determined speech sound is presented; or a peak latency that is associated with a template having a highest degree of matching, among previously-provided templates of N1 component waveforms, with the electroencephalogram signal.

The event-related potential processing section may take a summation of event-related potentials with respect to each consonant, or with respect to each group of speech sounds whose differences in reference latency is smaller than a predetermined value.

The annoyance judgment system may further comprise a result accumulating database configured to accumulate information indicating a result of annoyance judgment for the speech sound, wherein the result accumulating database may accumulate information indicating the result of annoyance judgment for the speech sound with respect to each speech sound, each consonant, or each group of speech sounds whose differences in reference latency is smaller than a predetermined value.

The annoyance judgment system may further comprise an acoustic aiding processing section configured to select a type of acoustic aiding process for the presented speech sound, and modify data of the speech sounds retained in the speech sound database based on the selected acoustic aiding process.

The annoyance judgment system may further comprise a switching section configured to switch between a calibration mode of determining reference latencies of negative components for the user and an assessment mode of assessing annoyance, wherein, in the calibration mode, the switching section may cause the presented-speech sound determination section to select a vowel, and calculate a reference latency for each speech sound based on a latency of the negative component for the vowel; and after switching to the assessment mode, the switching section may cause the annoyance judgment section to compare the peak latency of the negative component against the calculated reference latency.

In the calibration mode, when a vowel is selected by the presented-speech sound determination section, the switching section may set a latency of an N1 component for the vowel as a reference latency for the vowel, and calculate a reference latency for each consonant by adding a positive value which is adapted to a duration or intensity of a consonant portion to the reference latency for the vowel.

An annoyance judgment apparatus according to another embodiment disclosed herein comprises: a presented-speech sound determination section configured to determine a monosyllabic speech sound to be presented by referring to a speech sound database retaining a plurality of monosyllabic speech sounds such that, for each speech sound, the speech sound and a reference latency of an electroencephalogram negative component corresponding to the speech sound are retained in association; an annoyance judgment section configured to, in an electroencephalogram signal of a user measured by a biological signal measurement section, compare a peak latency of a negative component of the electroencephalogram signal in a range from 50 ms to 350 ms from a starting point, the starting point being a point in time at which the speech sound is presented to the user by an output section, against the reference latency corresponding to the determined speech sound that is retained in the speech sound database, and outputting a difference between the peak latency and the reference latency; and an acoustic aiding processing section configured to adjust the speech sound based on the difference output from the annoyance judgment section.

An annoyance judgment method according to another embodiment disclosed herein comprises the steps of: measuring an electroencephalogram signal of a user; determining a monosyllabic speech sound to be presented by referring to a speech sound database retaining a plurality of monosyllabic speech sounds such that, for each speech sound, the speech sound and a reference latency of an electroencephalogram negative component corresponding to the speech sound are retained in association; presenting the determined speech sound to the user; and judging annoyance of the output speech sound by comparing a peak latency of a negative component of the electroencephalogram signal in a range from 50 ms to 350 ms from a starting point, the starting point being a point in time at which the speech sound is presented, against the reference latency corresponding to the determined speech sound that is retained in the speech sound database.

A computer program according to another embodiment disclosed herein is a computer program, stored on a non-transitory computer-readable medium, to be executed by a computer mounted in an annoyance judgment system for speech sound listening, wherein the computer program causes the computer in the annoyance judgment system to execute the steps of: receiving an electroencephalogram signal of a user; determining a monosyllabic speech sound to be presented by referring to a speech sound database retaining a plurality of monosyllabic speech sounds such that, for each speech sound, the speech sound and a reference latency of an electroencephalogram negative component corresponding to the speech sound are retained in association; presenting the determined speech sound to the user; and judging annoyance of the output speech sound by comparing a peak latency of a negative component of the electroencephalogram signal in a range from 50 ms to 350 ms from a starting point, the starting point being a point in time at which the speech sound is presented, against the reference latency corresponding to the determined speech sound that is retained in the speech sound database.

An annoyance judgment system according to still another embodiment disclosed herein comprises: a biological signal measurement section configured to measure an electroencephalogram signal of a user; an audio input section configured to input an audio signal of an utterance by a specified speaker; an audio analysis section configured to output a trigger upon detecting a timing at which the audio signal is input, and analyzing a characteristic feature of the audio concerning a duration and an intensity of a consonant portion; a reference latency estimation section configured to, based on the characteristic feature analyzed by the audio analysis section, estimate a reference latency of a negative component; and an annoyance judgment section configured to judge annoyance by comparing a peak latency of a negative component of the electroencephalogram signal in a range from 50 ms to 350 ms from the trigger as a starting point against the reference latency estimated by the reference latency estimation section.

The annoyance judgment system may further comprise a character output section configured to output text information indicating a speech sound for the specified speaker to utter, wherein an audio signal of an utterance by the specified speaker is input to the audio input section based on the text information having been output from the character output section.

The character output section may further output information concerning a sound pressure indicating a loudness with which the specified speaker is to utter the monosyllabic speech sound; and an audio signal of an utterance by the specified speaker may be input to the audio input section based on the text information and information concerning sound pressure having been output from the character output section.

The annoyance judgment system may further comprise a presented-speech sound determination section configured to determine a speech sound for the specified speaker to utter by referring to a previously-provided speech sound list, wherein the character output section outputs text information indicating the speech sound determined by the presented-speech sound determination section.

The reference latency estimation section may estimate the reference latency of a negative component based on the characteristic feature analyzed by the audio analysis section and on the speech sound for the specified speaker to utter that is determined by the presented-speech sound determination section.

The reference latency estimation section may estimate the reference latency of a negative component by adding a predetermined positive value to previously-provided base latency, the predetermined positive value being adapted to a consonant duration or consonant intensity of the audio.

An annoyance judgment method according to still another embodiment disclosed herein comprises the steps of: inputting an audio signal of an utterance by a specified speaker; outputting a trigger upon detecting a timing at which the audio signal is input, and analyzing characteristic feature of the audio concerning a duration and an intensity of a consonant portion; estimating a reference latency of a negative component, based on the characteristic feature analyzed by the analyzing step; and judging annoyance by comparing a peak latency of a negative component of the electroencephalogram signal in a range from 50 ms to 350 ms from the trigger as a starting point against the reference latency estimated by the estimating step.

Hereinafter, with reference to the attached drawings, embodiments of an annoyance judgment system for speech sound listening according to the present disclosure will be described.

An annoyance judgment system for speech sound listening according to the present disclosure is used for making an assessment concerning, as a user state when listening to speech sounds, whether a user felt annoyed or not in speech sound listening, by utilizing his or her electroencephalogram. More specifically, the present system presents a monosyllabic speech sound as an audio, and assesses annoyance in speech sound listening, where an event-related potential of the user electroencephalogram which is measured based on audio presentation as a starting point is utilized as an index.

Now, the terminology used in the present specification will be described. An "event-related potential (ERP)" means a portion of an electroencephalogram (EEG), referring to a transient potential fluctuation in the brain which occurs in temporal relationship with an external or internal event. To "present an audio" means to output an auditory stimulation (also referred to as an "audio stimulation"). For example, an audio may be output through a loudspeaker. Note that the type of loudspeaker may be arbitrary. It may be a loudspeaker which is placed on the floor or on a stand, or may be loudspeakers in the form of headphones. However, in order to correctly perform an assessment, any loudspeaker needs to be able to accurately make an output at a designated sound pressure. "Assessment" may also be used in the sense of "judgment".

Through a speech sound intelligibility assessment and through a detailed analysis of the user state at the time of assessment, the inventors have found that an assessment of "annoyance", as a measure of how annoyed a user is, is needed. This will be specifically described below.

In a speech sound intelligibility assessment, an assessment is made as to whether each speech sound was aurally distinguished (◯) or not (X), and the number of speech sounds that have been successfully aurally distinguished is divided by the number of speech sounds subjected to assessment (i.e., 20 in the case of the 67S list). Therefore, the result does not reflect any user state when listening to speech sounds.

However, in actuality, there may be cases where an aural distinction is made in comfort as well as cases where an aural distinction is made in discomfort. A speech sound intelligibility assessment is a short-time assessment which takes place at a hearing aid shop. The fact as to whether the user feels annoyed or not is irrelevant to the assessment; therefore, unless it is so annoying that it is intolerable, the user will be willing to carry out the assessment task even if slightly annoyed.

However, in the case where a hearing aid is worn for long hours on a daily basis, it would be a burden to the user if he or she had to tolerate acoustic annoyance for a long time.

In view of these situations, the inventors have arrived at the thought that assessment needs to be made separately with respect to different user states when listening to speech sounds: when no "patience for annoyance" is needed; and when some "patience for annoyance" is needed. Since annoyance pertains to a process in the brain during speech sound listening, there is a possibility that it can be assessed through electroencephalogram measurement.

1. Experimental Outline

With a view to realizing annoyance judgment in speech sound listening, the inventors have conducted the following experiment for identifying an electroencephalogram characteristic component which reflects annoyance.

On the premise of presenting a monosyllabic speech sound in the form of an audio and asking a user to think of a speech sound corresponding to the audio, an electroencephalogram measurement experiment was conducted where an event-related potential was measured based on audio presentation as a starting point. In the experiment, it was asked that subjective reports on annoyance in speech sound listening be made. Then, based on the subjective reports on annoyance, an arithmetic mean of event-related potentials was taken. Note that the step of asking to think of a speech sound corresponding to an audio is not essential in annoyance judgment.

The inventors have thus found that, in the event-related potential based on audio presentation as a starting point, a negative component (N1 component) at a latency of about 200 ms will have its latency decreased as the annoyance with respect to the audio increases. They have further found that the latency of the N1 component varies depending on differences in characteristic features, e.g., consonant duration and consonant intensity, from speech sound to speech sound. "Latency" represents, based on the point in time of presenting an audio stimulation as a starting point, an amount of time which lapses before a positive component or negative component peak appears.

From these findings, the inventors have found that annoyance judgment in speech sound listening can be made based on the latency of a negative component (N1 component). With this technique, as a user state when listening to speech sounds, an assessment as to whether the user was being annoyed can be made in an objective and quantitative manner for each speech sound.

These will be described in more detail below. Firstly, an electroencephalogram measurement experiment which was conducted by the inventors in order to realize annoyance judgment in speech sound listening will be described. Thereafter, as an embodiment, an outline of an annoyance judgment apparatus for speech sound listening which assesses comfortableness of speech sound listening, as well as a construction and operation of an annoyance judgment system for speech sound listening which includes the annoyance judgment apparatus for speech sound listening, will be described.

2. Electroencephalogram Measurement Experiment

In the electroencephalogram measurement experiment, a relationship between the subjective reports on annoyance which were acquired after audio presentation and an event-related potential based on the audio as a starting point was examined. Hereinafter, with reference to FIG. 1 to FIG. 6, the experimental setting and experimental results of the electroencephalogram measurement experiment will be described.

Thirteen undergraduate or graduate students with normal hearing participated in the experiment.

FIG. 1 shows the experimental procedure of the electroencephalogram measurement experiment in outline. First, a monosyllabic audio was presented in Procedure A. The particulars of the presented audios will be described later. Next, in Procedure B, each participant was allowed to hear an audio, and asked to write down a hiragana corresponding to the audio as he or she heard it. The conditions of the presented audios were kept unvaried, while only the speech sound type was varied. Procedures A and B were repeated five times (5 trials). Then, in Procedure C, the participant was asked to make a subjective evaluation concerning annoyance and the like with respect to each audio that was presented in Procedure A. The subjective evaluation was based on a visual analog scale (100-step evaluation), and was made by using a touch panel. This was repeated 12 blocks, where 1 block consisted of Procedure A to Procedure C as above (totaling 60 trials). For each block, the sound pressure and distortion conditions of the presented audios were varied in random order.

FIG. 2 is a flowchart showing a procedure corresponding to one block.

At step S11, a monosyllabic audio is presented to an experimental participant.

At step S12, the participant thinks of a corresponding text character upon hearing the monosyllabic audio.

At step S13, the participant writes down the text character corresponding to the audio as he or she heard it.

At step S14, the number of times that the audios have been presented is counted. While the number of presentations is equal to or less than 4, the process returns to step S11. When the number of presentations reaches 5, the process proceeds to step S15, where the number of presentations is reset.

At step S15, the participant answers with a subjective perception of the audio which was heard at step S11.

From among unvoiced consonants which are supposed to induce mistakes in aural comprehension, 8 sounds (キ (ki), ク (ku), シ (shi), ス (su), タ (ta), テ (te), ト (to), ハ (ha)) in the 67S list as proposed by the Japan Audiological Society were selected as the speech sounds to be presented as stimulations. Speech sounds with adjusted frequency gains were used, thus to control annoyance for participants with normal hearing. A "frequency gain" refers to a gain (i.e., a circuit gain or rate of amplification) for each of a number of frequency bands.

For frequency gain adjustment, three sound pressure levels (Large, Middle, Small) X two distortion levels (Flat, Distorted) were employed, totaling six conditions, as are detailed in (1) to (6) below. In the present specification, large sound pressure and flat (no distortion) conditions may be referred to as LF condition (an acronym of Large and Flat), for example.

(1) LF (Large Flat) condition: the gain was increased by 20 dB across entire frequency band, meant as an audio which had a large sound pressure and was easy to aurally distinguish. (2) LD (Large Distorted) condition: the gain was uniformly increased by 20 dB relative to the MD condition, meant as an audio which had a large sound pressure but was difficult to aurally distinguish. (3) MF (Middle Flat) condition: the frequency gain was not modified, meant as an audio which had a large sound pressure and was easy to aurally distinguish. (4) MD (Middle Distorted) condition: from an audio of the LF condition, the gain at frequencies of 250 Hz to 16 kHz was gradually adjusted (decreased) to −30 dB, meant as an audio which was difficult to aurally distinguish. (5) SF (Small Flat) condition: the gain was decreased by 20 dB across the entire frequency band, meant as an audio which had a small sound pressure but was easy to aurally distinguish. (6) SD (Small Distorted) condition: the gain was uniformly decreased by 20 dB relative to the MD condition, meant as an audio which had a small sound pressure and was difficult to aurally distinguish.

Figures 3A, 3B:
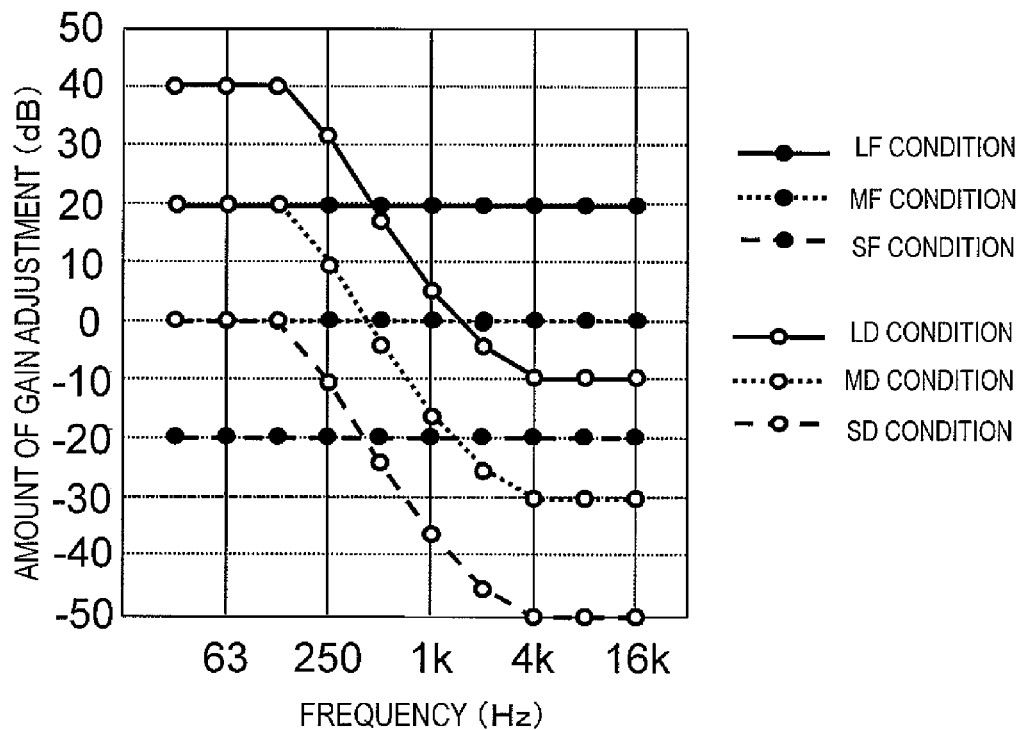
FIG. 3A is a diagram showing sound pressure levels measured with a sound-level meter under different conditions.
FIG. 3B is a diagram showing amounts of gain adjustment for different frequencies under each of six conditions.

FIG. 3A shows classification of six conditions concerning sound pressure and distortion. FIG. 3B shows amounts of gain adjustment for different frequencies. The reason why the frequency gain for the high-frequency band was decreased is in order to reproduce a typical pattern of hypacusia of elderly people, i.e., gradual high tone loss. The audio stimulations were presented from a loudspeaker with flat frequency characteristics.

Each electroencephalogram was recorded from electrodes placed at the Fz, Cz, Pz, C3, and C4 (International 10-20 system) on the scalp, the right and left temples, and above and below the right eye, on the basis of the right mastoid. A "mastoid" is a protrusion of the cranium below the hind root of an ear. FIG. 4A shows electrode positions according to the International 10-20 system (10-20 System), whereas FIG. 4B shows electrode positioning as to how electrodes were worn in the present experiment. The sampling frequency was 200 Hz, and the time constant was 1 second. It was subjected to a 0.05 to 20 Hz digital band-pass filter off-line. As an event-related potential in response to an audio presentation, a waveform from −200 ms to 1000 ms was cut out based on the point of audio presentation as a starting point. Herein, "−200 ms" signifies a point in time which is 200 milliseconds before the point of audio presentation.

Hereinafter, distribution of results of subjective evaluation and threshold value setting will be described.

First, results of subjective evaluation will be described. Based on the results of subjective evaluation, "annoying/not annoying" was labeled relative to a threshold value which was determined for each participant based on a method describe below. Hereinafter, these subjective evaluation labels will be treated as the user states when listening to speech sounds.

Figure 5:
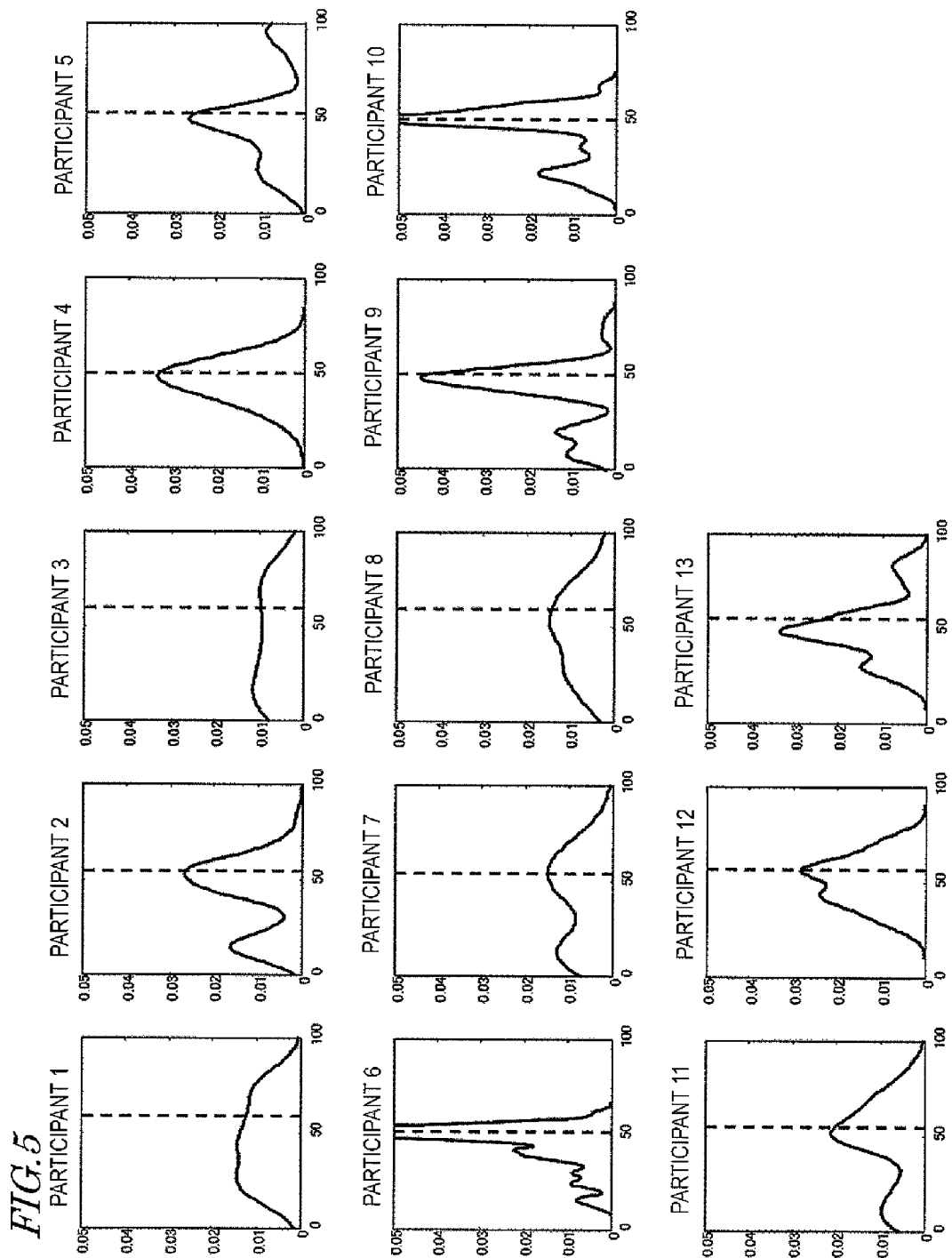
FIG. 5 is a diagram showing results of subjective reporting on annoyance made by a visual analog scale.

FIG. 5 shows results of subjective evaluation of different participants concerning annoyance. The horizontal axis represents a subjective perception evaluation value (1 to 100 on the visual analog scale), whereas the vertical axis represents a ratio (0 to 1) obtained by dividing the frequency distribution by the total number of trials. Each graph of FIG. 5 shows a proportion within all trials.

Each solid line in FIG. 5 shows a distribution of results of subjective evaluation, whereas each broken line shows a threshold value at which subjective evaluations ("annoying/not annoying") are split. The inventors determined the threshold value based on the ordinal ranks of evaluation results (i.e., 1 to 100 on the visual analog scale) of each individual person. Specifically, within each individual, the inventors defined those evaluation values whose ordinal rank are within the largest third as "annoying", and the rest as "not annoying", thus setting the threshold value therebetween. Herein, identical evaluation results were treated as pertaining to the same subjective evaluation.

Hereinafter, as event-related potential results, a result of taking an arithmetic mean based on the "annoying"/"not annoying" criteria, as labeled based on results of subjective evaluation, will be described.

Figure 6:
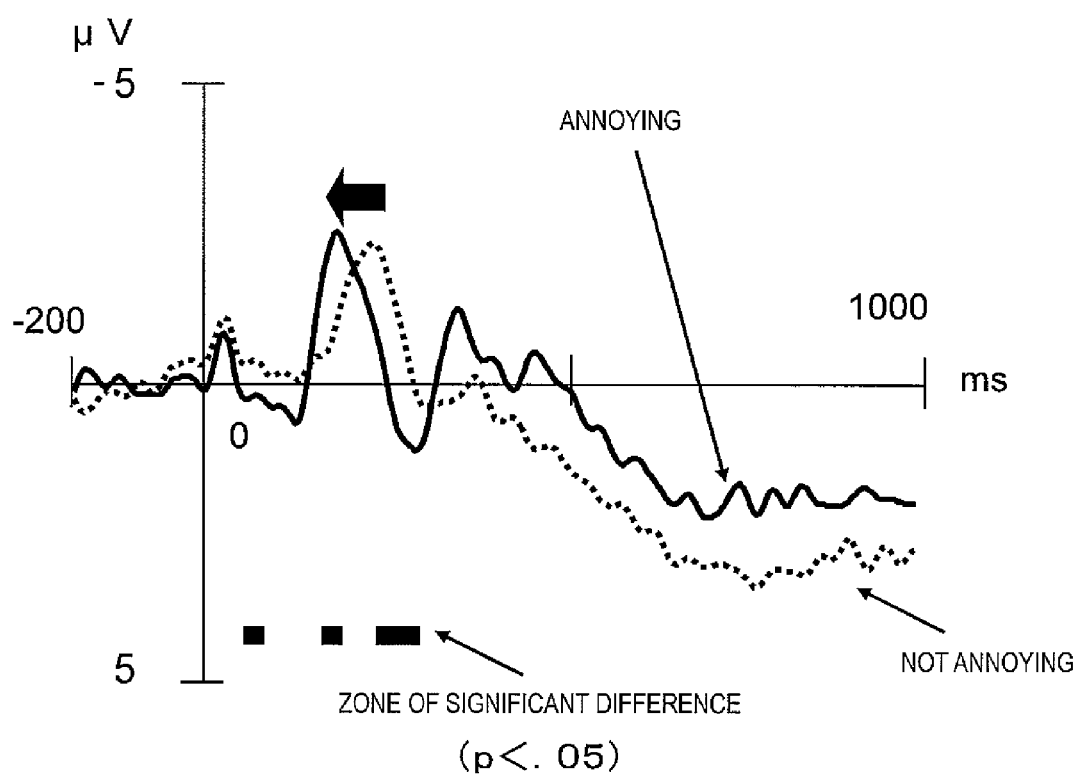
FIG. 6 is a diagram showing waveforms obtained by taking an arithmetic mean of event-related potentials at Pz based on a point of audio presentation as a starting point, for each of different subjective evaluations concerning annoyance.

FIG. 6 shows waveforms obtained by taking an arithmetic mean of event-related potentials at the parietal (Pz) based on a point of presenting an audio stimulation as a starting point. Specifically, FIG. 6 shows waveforms each obtained by taking a total arithmetic mean according to the "annoying/not annoying" criterion as labeled with the above method. An arithmetic mean was taken based on the subjective evaluations concerning annoyance for respective blocks, under the six conditions in the above-described measurement experiment. In FIG. 6, the horizontal axis represents time in units of ms, whereas the vertical axis represent potential in units of μV. As is clear from the scales shown in FIG. 6, the lower direction in the graph corresponds to plus (positive), and the upper direction corresponds to minus (negative). In FIG. 6, a solid line represents a total arithmetic mean waveform in the case of "annoying", and a broken line represents a total arithmetic mean waveform in the case of "not annoying".

It can be seen from FIG. 6 that a negative component (N1 component) which is induced at a latency of about 200 ms has a shorter latency in the case of "annoying" (solid line) than in the case of "not annoying" (broken line). The latency of the N1 component of each participant was 195 ms in the case of "annoying", and 240 ms in the case of "not annoying". As a result of t-testing the latencies, a significant difference was recognized (p<0.05). Thus, it was concluded that the latency was shorter in the "annoying" case than in the "not annoying" case. It can be said that the latency of an N1 component based on presentation of an audio stimulation (hereinafter "audio presentation") as a starting point reflects annoyance as a subjective perception of the user, and can be used as an index of annoyance in speech sound listening.

It is known from conventional studies using a pure tone (tone pip, tone burst) that the latency and amplitude of an N1 component in response to an auditory stimulation change in accordance with the intensity and rise time of the sound stimulation (see Suzuki et al., 1985, CHOSEI NOKANH- ANNO—SONOKISOTO RINSHO—, or "Auditory Brain Stem Response—Its Basics And Clinical Applications—, pp. 384-385). Specifically, as the stimulation sound increases in intensity, the latency decreases and the amplitude (i.e., an absolute value of the difference N1 component-P2 component) increases. Moreover, the amplitude decreases as the rise time of the stimulation sound increases.

Figure 7:
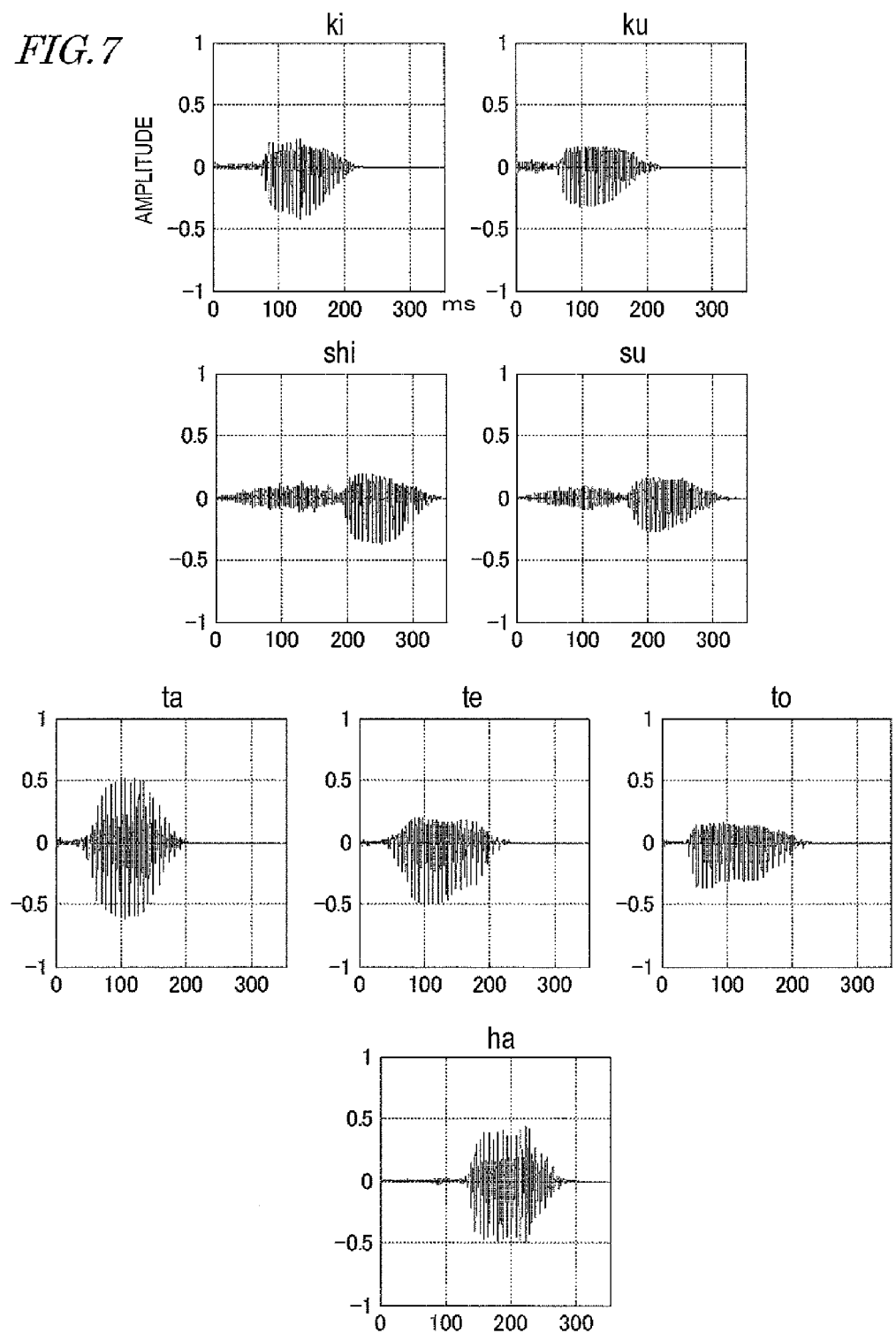
FIG. 7 shows audio waveforms under the MF condition that were presented in an experiment.

In the present experiment, speech sounds were used as auditory stimulations. FIG. 7 shows exemplary audio waveforms under the MF condition (8 speech sounds: キ (ki), ク (ku), シ (shi), ス (su), タ (ta), テ (te), ト (to), ハ (ha)) that were used in the present experiment. As can be seen from FIG. 7, each audio differs in the duration and intensity of the consonant portion and the intensity and rise time of the vowel portion. For example, attention may be paid to the duration of the consonant portion (consonant duration). A consonant duration is a length of time which elapses after a point of occurrence of a waveform (0 ms) until a relatively large rise emerges in the waveform. More specifically, a consonant duration is a length of time elapsing until a vowel rises. The consonant duration was about 80 ms for the ka-row (キ (ki), ク (ku)), about 170 ms for the sa-row (シ (shi), ス (su)), about 40 ms for the ta-row (タ (ta), テ (te), ト (to)), and about 130 ms for the ha-row (ハ (ha)). Moreover, for example, the intensity of the consonant portion was stronger in the sa-row than in the ka-, ta-, and ha-rows. Notwithstanding these significant row-to-row differences in the audio waveform, it can also be seen that the characteristic feature of the overall waveform is kept alike within each given row.

Note that the ka-row includes speech sounds which begin with "k": specifically, ka, ki, ku, ke, and ko. The sa-row includes speech sounds which begin with specifically, sa, shi, su, se, and so. The ta-row includes speech sounds which begin with "t": specifically, ta, ti(chi), tu(tsu), te, and to.

From the knowledge on pure tone stimulations from conventional studies, and the differences in audio waveform between speech sounds shown in FIG. 7, there is a possibility that the latency and amplitude of the N1 component for a speech sound may differ from speech sound to speech sound. If a characteristic feature of the presented speech sound audio is the cause of a latency fluctuation in the N1 component, the latency of the N1 component will fluctuate irrespective of "annoyance". Therefore, incorrect assessments may be made, e.g., assessing a non-annoying audio to be annoying, or assessing an annoying audio to be not annoying.

Therefore, the inventors have taken an arithmetic mean for each given row, within which the audio waveforms share similar characteristic features. By taking an arithmetic mean for each row, a certain number of times of arithmetic mean that is needed for the analysis of N1 component latency is attained. Then, from the arithmetic mean waveform result of each row, the influences that differing characteristic features of audio stimulations exert on the N1 component latency were examined. In order to clarify the relationship between sound pressure and N1 component latency, an arithmetic mean was taken for each sound pressure, irrespective of the presence or absence of distortion.

FIGS. 8A to 8C show exemplary arithmetic mean results for different rows. FIGS. 8A to 8C show results for the ta-row (タ (ta), テ (te), ト (to)), the ha-row (ハ), and the sa-row (シ (shi), ス (su)), respectively. In FIGS. 8A to 8C, the horizontal axis represents time in units of ms, whereas the vertical axis represents potential in units of μV.

As is clear from the scales shown in FIGS. 8A to 8C, the lower direction in the graph corresponds to plus (positive), and the upper direction corresponds to minus (negative). In each of FIGS. 8A to 8C, a thick solid line represents a total arithmetic mean waveform under a Large condition (85 dB), a broken line represents a total arithmetic mean waveform under a Middle condition (65 dB), and a thin solid line represents a total arithmetic mean waveform under a Small condition (45 dB). In FIGS. 8A to 8C, each ○ symbol indicates an N1 component. As the N1 component, a minimum value in a zone from 0 ms to 500 ms is taken, for example. In order to show temporal correspondence between the audio waveforms and the electroencephalograms, audio waveforms of speech sounds "タ (ta)", "ハ (ha)", and "シ (shi)" are indicated in FIGS. 8A to 8C as representatives of the respective rows, with their starting points being aligned. It can be seen from FIGS. 8A to 8C that, in each row, the N1 component latency decreases as the sound pressure increases. It can also be seen that under the Large condition of FIG. 8C, the N1 component has its peak before the vowel portion rises.

Figure 9:
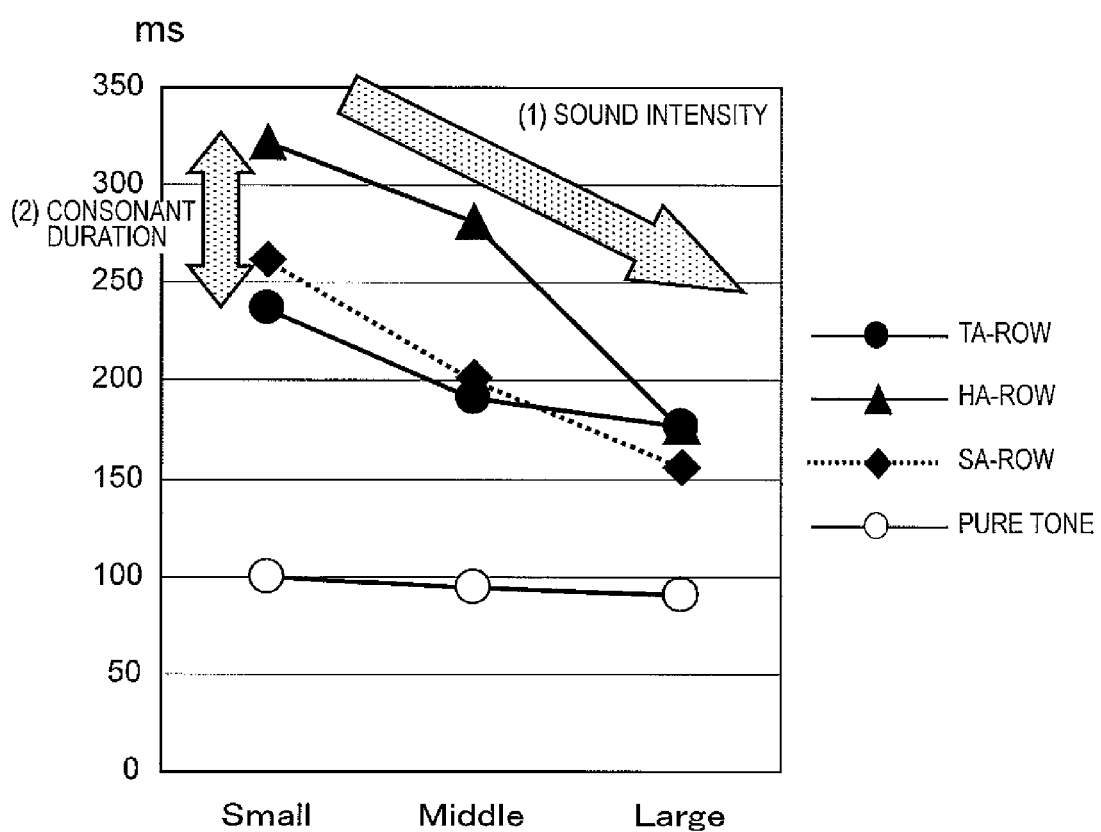
FIG. 9 is a diagram showing changes in the latency of an N1 component for each group of speech sounds sharing the same consonant depending on sound pressure, and changes in the latency of an N1 component for a pure tone depending on sound pressure in conventional studies.

FIG. 9 shows exemplary changes in the latency of each N1 component with sound pressure, as found in the present experiment. FIG. 9 also shows changes in the latency of an N1 component for a pure tone with sound pressure, as found in a conventional study. FIG. 9 indicates the following characteristic features regarding (1) sound intensity and (2) consonant duration. Regarding (1) sound intensity, it can be seen that the N1 component latency decreases in each row as the sound pressure increases. Regarding (2) consonant duration, it can be seen through a comparison between the result for the ta-row and the result for the ha-row that the N1 component latency differs depending on consonant duration.

The aforementioned sound intensity and consonant duration will be respectively discussed below.

First, the latency-decreasing characteristics of the N1 component associated with increasing sound pressure of the speech sound audio will be discussed. According to conventional studies, it is known in the case of a pure tone that the N1 component latency only has a decrease of 10 ms for a similar sound pressure increase of 40 dB. On the other hand, upon using the experimental results of the inventors to analyze the decrease in N1 component latency that is associated with an increase in the sound pressure of a speech sound audio, it was found that a decrease of about 100 ms occurs on average among the sa-row, the ta-row, and the ha-row, in response to a sound pressure increase of 40 dB (i.e., from 45 dB to 85 dB). This indicates differing latency-decreasing characteristics of the N1 component between pure tones and speech sounds. Thus, it can be said that the latency-decreasing characteristics associated with an increase in the sound pressure of the speech sound audio had never been clarified before the experiment conducted by the inventors.

Next, the latency-decreasing characteristics of the N1 component associated with consonant duration will be discussed. For example, as shown in FIG. 7, the consonant durations of the ta-row and the ha-row are about 40 ms and about 130 ms, respectively, resulting in a difference of about 90 ms. The latencies for the ta-row and the ha-row under the Small condition are 236 ms and 322 ms, thus conserving a difference of about 90 ms. Thus, it is considered that these N1 components are induced in response to the rise of the vowel. On the other hand, in the sa-row having a stronger consonant intensity than any other row, consonant duration exerts a different influence. The consonant duration of the sa-row is about 170 ms, which is longer than the consonant duration (about 130 ms) of the ha-row; however, the N1 component latency is shorter for the sa-row than for the ha-row, under all sound pressure conditions. Moreover, the N1 component latency for the sa-row under Large condition is 156 ms, which is shorter than the consonant duration of the sa-row itself.

It can be said from these results that, when the consonant duration is longer than a predetermined time (e.g., about 100 ms) and the consonant intensity is strong, an N1 component will be induced in response to the consonant.

Figure 10:
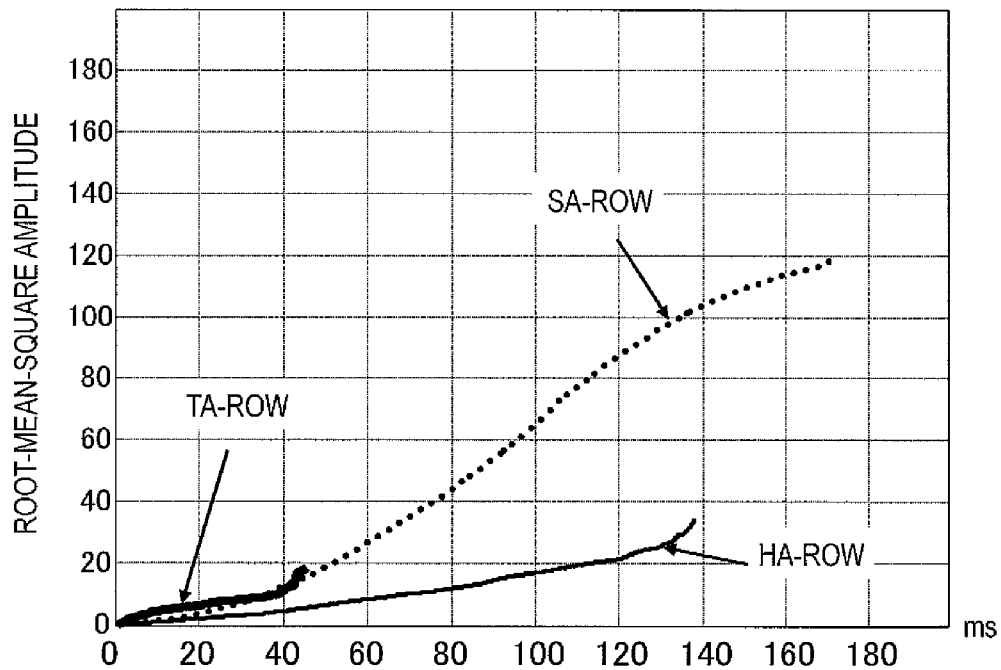
FIG. 10 is a diagram showing, as an illustration of consonant intensity of speech sound audios which are presented as stimulations, sums of root-mean-square amplitude (up to that point in time) of their respective consonant portions under the MF condition.

FIG. 10 shows, as an illustration of consonant intensity of speech sound audios which are presented as stimulations, sums of root-mean-square amplitude (up to that point in time) of their respective consonant portions under the MF condition. It can be seen from FIG. 10 that the consonant portion has a higher intensity in the sa-row than in any other speech sound. The "consonant intensity" means an amplitude level of an audio waveform in a time slot corresponding to its consonant portion. The consonant intensity may be determined from a root-mean-square value of the amplitude of the consonant portion, for example.

Figure 11:
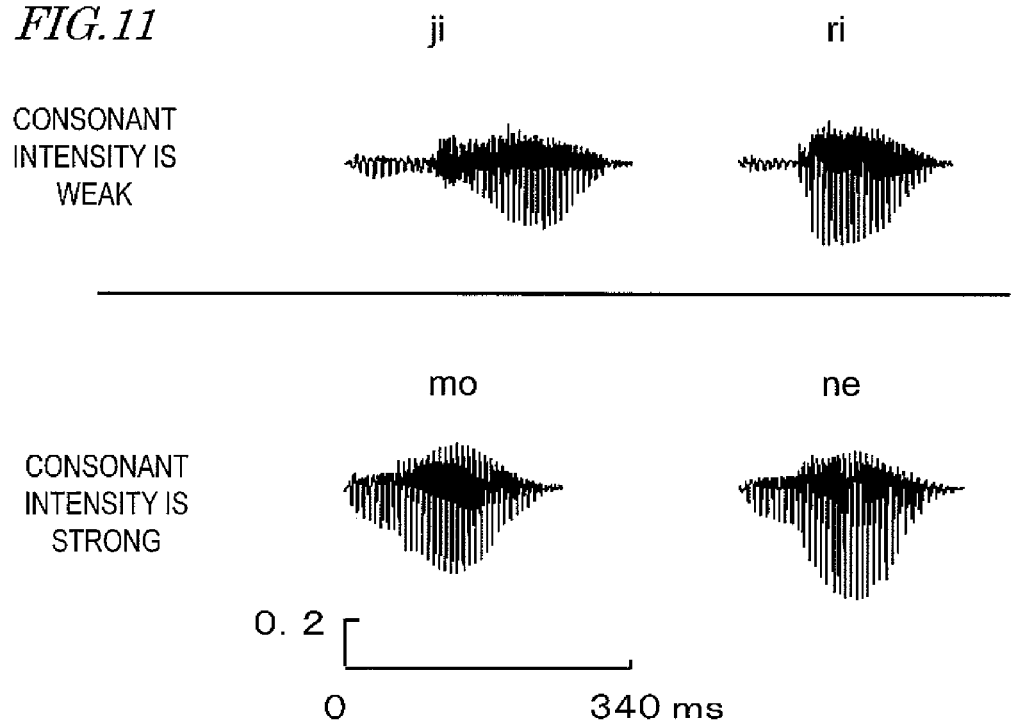
FIG. 11 is a diagram showing examples of audio waveforms of consonants having a weak consonant intensity and those having a strong consonant intensity.

FIG. 11 shows examples of audio waveforms of consonants having a weak consonant intensity and those having a strong consonant intensity. It is indicated that the consonant intensity is stronger in the ma-row "モ (mo)" and the na-row "ネ (ne)" than in the za-row "ジ (ji)" and the ra-row "リ (ri)". Other than the sa-row, the speech sounds in the ma-row, the na-row, the ya-row, the wa-row, and the ga-row may be said to have a strong consonant intensity, for example.

Therefore, for a speech sound whose consonant portion has a strong intensity, if no N1 component is induced in response to its consonant portion, but an N1 component is induced only in response to its vowel portion (i.e., the N1 component latency is significantly lagged beyond expectation), it may be determined that the consonant portion was not heard.

Thus, it has become clear through the electroencephalogram measurement experiment that there is an electroencephalogram component that reflects a user's subjective evaluation concerning annoyance in speech sound listening. Specifically, it has been found that a negative potential having a peak at a latency of about 200 ms reflects annoyance. It has also been found that the N1 component latency varies from speech sound to speech sound, because of influences of the differing audio waveforms.

The latency of the aforementioned N1 component at the parietal (Pz) for each subjective evaluation concerning annoyance (FIG. 6) may be defined as a point in time at which the component takes the smallest potential in the zone in question. Alternatively, templates may be created from the waveforms of typical N1 components, and a peak point of the N1 component of one template that has the highest degree of matching with the measured waveform may be regarded as the latency. Note that the N1 component latency is identifiable through a method of making a comparison against a predetermined threshold value concerning latency, or the like. The threshold value and template may be those of a typical user as previously stored, or may be generated for each individual person. In this experiment, arithmetic means were taken from the data of 13 participants in order to confirm the fact that components which reflect the subjective perception concerning annoyance appear in an event-related potential based on a point of audio presentation as a starting point. However, depending on the method of characteristic amount extraction (e.g., wavelet transformation of the waveform) or the method of identification (e.g., support vector machine learning), identification of a negative component is possible with no summations or only a small number of summations.

In the present specification, in order to define a component of an event-related potential, a point in time after the lapse of a predetermined time since a given point is expressed by referring to a "latency of about 200 ms", for example. This means possible inclusion of a range around the specific point of 200 ms in time. Generally speaking, there are 30 to 50 ms of differences (shifts) in event-related potential waveform between individuals, according to table 1 on p. 30 of "JISHOUKANRENDENI (ERP) MANYUARU—P300 WO CHUSHINNI—(or "Event-Related Potential (ERP) Manual—mainly concerning P300—"), edited by Kimitaka KAGA et al., Shinohara Shuppan Shinsha, 1995)". Therefore, the terms "about X ms" and "near X ms" mean that a breadth of 30 to 50 ms may exist before or after X ms (e.g., 300 ms±30 ms, 750 ms±50 ms). Moreover, as mentioned above, the N1 component latency varies depending on the characteristic feature of the speech sound audio. Therefore, in order to at least account for the varying consonant duration (from 0 ms (vowel) to about 200 ms (consonant)), the aforementioned positive component is preferably treated as having a broader breadth, e.g., a breadth of about 150 ms on each of the earlier side and the later side. Accordingly, in the present embodiment, a "latency of about 200 ms" is meant to indicate a latency falling within the range from 50 ms to 350 ms.

Thus, the inventors have found through their electroencephalogram measurement experiment that, in an event-related potential based on the point of audio presentation as a starting point, a negative component at a latency of about 200 ms (N1 component) reflects annoyance. Therefore, based on an event-related potential in response to an audio presentation (audio stimulation) as an index, a subjective evaluation of annoyance in speech sound listening can be realized.

Figures 12, 13:
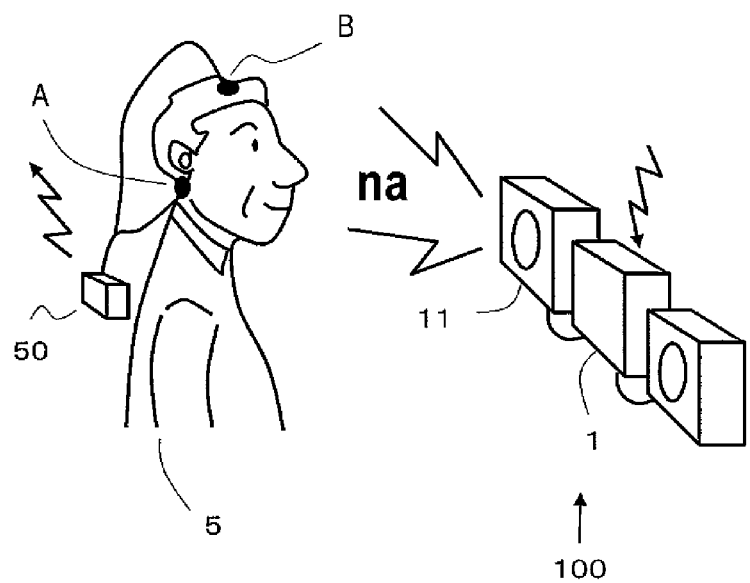
FIG. 12 is a diagram showing correspondence between results of latency comparison of the N1 component and results of annoyance judgment.
FIG. 13 is a diagram showing a construction and an environment of use for an annoyance judgment system 100 for speech sound listening according to Embodiment 1.

FIG. 12 shows correspondence between N1 component latency and annoyance judgment, as compiled by the inventors. If the N1 component latency is shorter than a predetermined threshold value, an "annoying" judgment is made. If the N1 component latency is longer than the predetermined threshold value a "not annoying" judgment is made.

Note that a "negative component" would generally mean any potential which is smaller than 0 μV. However, in the present specification, in order to distinguish whether the user has felt "annoyed" or not, not only the presence or absence of a "negative" component, but also the latency of the negative component being longer or shorter than a predetermined threshold value is considered. Note that, throughout the present specification, the case where the latency exactly equals the predetermined threshold value may be judged as indicating either that "the negative component is present" or that "the negative component is absent", depending on the application. Specific examples of the threshold value will be described later.

Hereinafter, an annoyance judgment system for speech sound listening according to embodiments of the present disclosure will be described. The annoyance judgment system for speech sound listening sequentially presents monosyllabic speech sounds in the form of audios, and determines annoyance in speech sound listening, by relying on the latency of a negative component in an event-related potential based on the point of audio presentation as a starting point. This is unprecedentedly realized by the findings of the inventors.

Embodiment 1

Hereinafter, the annoyance judgment system for speech sound listening will be first described in outline. Thereafter, the construction and operation of an annoyance judgment system for speech sound listening which includes the annoyance judgment apparatus for speech sound listening will be described.

The annoyance judgment system for speech sound listening of the present embodiment, presents audios, and an event-related potential is measured based on each point of audio presentation as a starting point. Then, a negative component at a latency of about 200 ms is detected, and annoyance in speech sound listening is judged.

In the present embodiment, a probe electrode is placed at the parietal (Pz), and a reference electrode was placed at the right or left mastoid, and an electroencephalogram was measured as a potential difference between the probe electrode and the reference electrode. Note that the levels and polarities of the characteristic components of the event-related potential may vary depending on the position at which the electrode for electroencephalogram measurement is attached, and the manner in which the reference electrode and the probe electrode are set. However, based on the following description, those skilled in the art would be able to detect a characteristic component of the event-related potential and make a speech sound intelligibility assessment by making appropriate modifications depending on the specific reference electrode and probe electrode. Any such variant is encompassed within the present disclosure.

In the above description of the electroencephalogram measurement experiment, the relative strength of the frequency gain is experimentally varied for participants with normal hearing, thus simulating the hearing of a person suffering from hypacusia. However, when conducting an assessment for a person suffering from hypacusia, there is no particular need to present speech sounds that are difficult to aurally distinguish. In the present embodiment, it is assumed that audios which have been adjusted with an optimum gain for each frequency are presented, based on a fitting theory from audiograms of people suffering from hypacusia that were measured in advance. Note that, in the case where an assessment is made while the user is wearing a hearing aid, adjustment for the presented audio is unnecessary.

FIG. 13 shows a construction and an environment of use for an annoyance judgment system 100 for speech sound listening according to the present embodiment. The annoyance judgment system 100 for speech sound listening is exemplified so as to correspond to a system construction of Embodiment 1 described later.

The annoyance judgment system 100 for speech sound listening includes an annoyance judgment apparatus 1 for speech sound listening, an audio output section 11, and a biological signal measurement section 50. The biological signal measurement section 50 is connected to at least two electrodes A and B. Electrode A is attached at a mastoid of the user 5, whereas electrode B is attached at the parietal (so-called Pz) on the scalp of the user 5.

The annoyance judgment system 100 for speech sound listening presents a monosyllabic speech sound to the user 5 in the form of an audio at a certain sound pressure, and determines whether the latency of an N1 component is shorter than a predetermined threshold value or not, in an electroencephalogram (event-related potential) from the user 5 which is measured based on the point of audio presentation as a starting point. Then, based on the presented audio and the result of distinction as to the latency of the N1 component, it is judged as to whether the user felt annoyed in speech sound listening.

An electroencephalogram from the user 5 is acquired by the biological signal measurement section 50 based on a potential difference between electrode A and electrode B. The biological signal measurement section 50 sends information corresponding to the potential difference (electroencephalogram signal) to the annoyance judgment apparatus 1 for speech sound listening in a wireless or wired manner. FIG. 13 illustrates an example where the biological signal measurement section 50 wirelessly sends this information to the annoyance judgment apparatus 1 for speech sound listening.

The annoyance judgment apparatus 1 for speech sound listening performs sound pressure control of the audio used for annoyance judgment in speech sound listening, controls presentation timing of the audio, and presents an audio via the audio output section 11 (e.g., loudspeakers) to the user 5.

Figure 14:
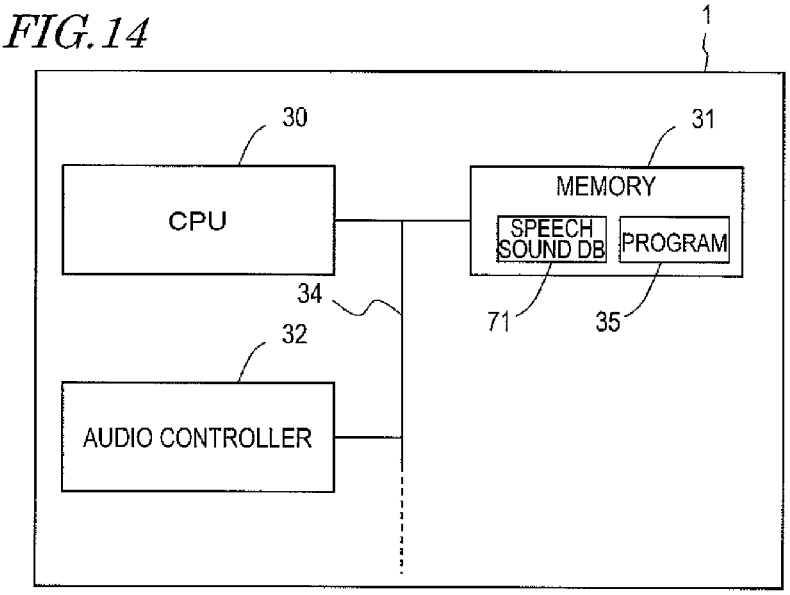
FIG. 14 is a diagram showing the hardware construction of an annoyance judgment apparatus 1 for speech sound listening according to Embodiment 1.

FIG. 14 shows a hardware construction of the annoyance judgment apparatus 1 for speech sound listening according to the present embodiment. The annoyance judgment apparatus 1 for speech sound listening includes a CPU 30, a memory 31, and an audio controller 32. These elements are interconnected via a bus 34 so that data exchange among them is possible.

The CPU 30 executes a computer program 35 which is stored in the memory 31. A processing procedure as illustrated by a subsequently-described flowchart is described in the computer program 35. In accordance with the computer program 35, the annoyance judgment apparatus 1 for speech sound listening performs a process of controlling the entire annoyance judgment system 100 for speech sound listening, by utilizing a speech sound database (DB) 71 which is also stored in the same memory 31. This process will be described in detail later.

In accordance with instructions from the CPU 30, the audio controller 32 generates an audio to be presented, and outputs the generated audio signal to the audio output section 11 at a designated sound pressure.

Note that the annoyance judgment apparatus 1 for speech sound listening may be implemented as a piece of hardware (e.g., a DSP) consisting of a semiconductor circuit having a computer program incorporated therein. Such a DSP can realize all functions of the aforementioned CPU 30, memory 31, and audio controller 32 on a single integrated circuit.

The aforementioned computer program 35 may be distributed on the market in the form of a product recorded on a storage medium such as a CD-ROM, or transmitted through telecommunication lines such as the Internet. Upon reading the computer program 35, a device having the hardware shown in FIG. 14 (e.g., a PC) is able to function as the annoyance judgment apparatus 1 for speech sound listening according to the present embodiment. Note that the speech sound DB 71 does not need to be stored in the memory 31, but may be stored on a hard disk (not shown) which is connected to the bus 34.

Figure 15:
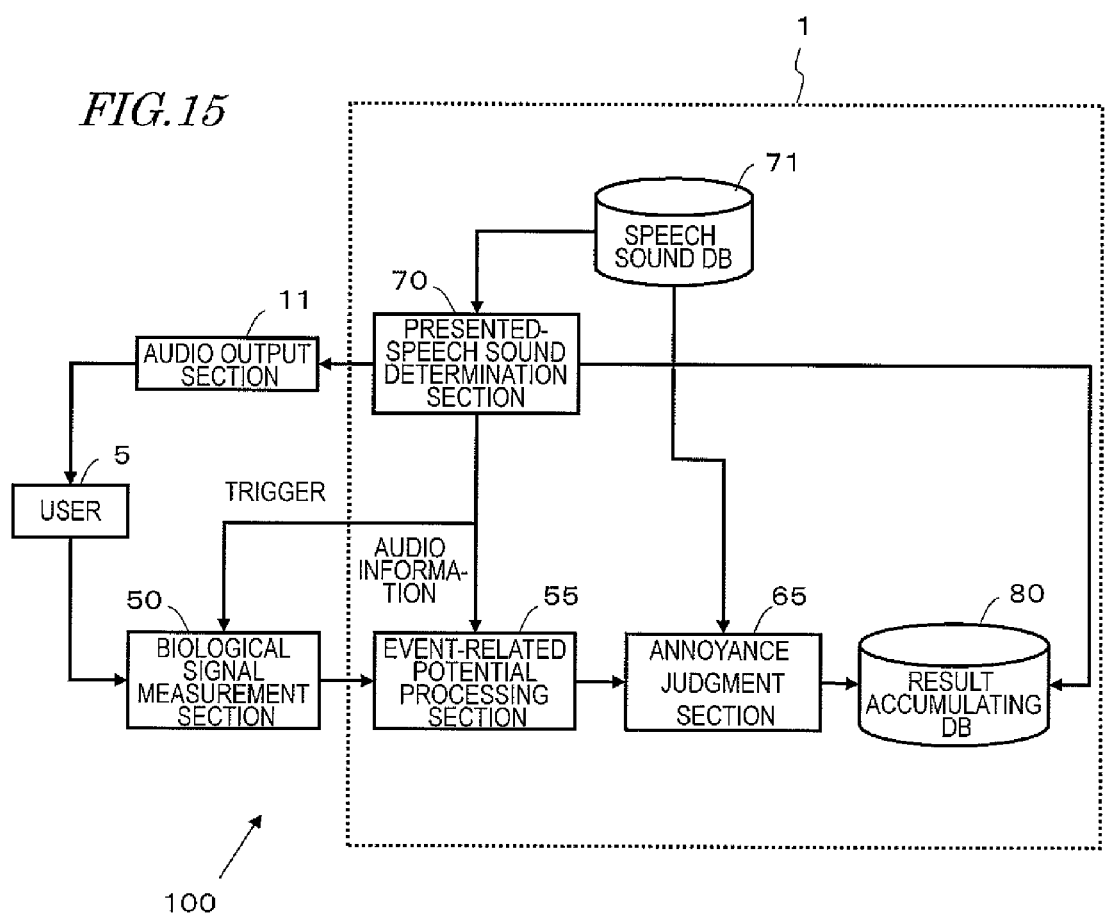
FIG. 15 is a diagram showing the functional block construction of the annoyance judgment system 100 for speech sound listening according to Embodiment 1.

FIG. 15 shows a functional block construction of the annoyance judgment system 100 for speech sound listening of the present embodiment. The annoyance judgment system 100 for speech sound listening includes the audio output section 11, the biological signal measurement section 50, and the annoyance judgment apparatus 1 for speech sound listening. FIG. 15 also shows detailed functional blocks of the annoyance judgment apparatus 1 for speech sound listening. Specifically, the annoyance judgment apparatus 1 for speech sound listening includes an event-related potential processing section 55, an annoyance judgment section 65, a presented-speech sound determination section 70, a speech sound DB 71, and a result accumulating DB 80. The user 5 block is illustrated for ease of explanation.

The respective functional blocks (except the speech sound DB 71) of the annoyance judgment apparatus 1 for speech sound listening correspond to functions which are realized by the CPU 30, the memory 31, and the audio controller 32 as a whole upon executing the program which has been described in conjunction with FIG. 14.

Figure 16:
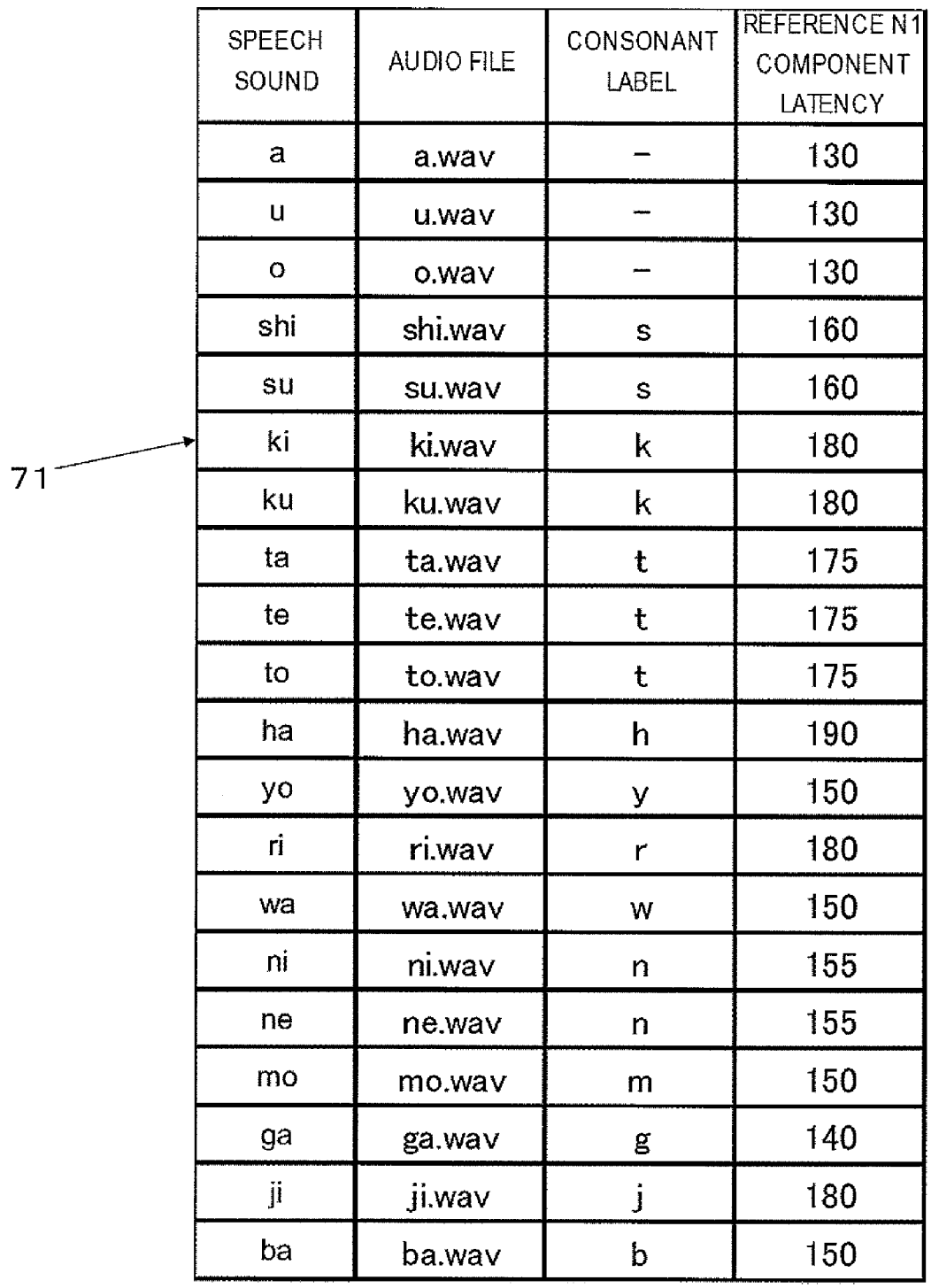
FIG. 16 is a diagram showing an example of a speech sound DB 71.

The speech sound DB 71 is a database of speech sounds which is provided for performing annoyance judgment in speech sound listening. FIG. 16 shows an exemplary speech sound DB 71 in the case where 20 speech sounds of the 67S list are to be used as test speech sounds, for example. In the speech sound DB 71 shown in FIG. 16, an audio file and a consonant label of each speech sound for presentation, as well as the reference latency of an N1 component for each speech sound, are retained in association. Preferably, the reference N1 component latency of each speech sound is a length which is adapted to the duration or intensity of the consonant that is contained in the speech sound. The audio files may be standard test audios of the 20 words in the 67S list, or audio recordings of the voice of a person who is a main partner of conversation through a hearing aid, for example. As for the stored audios, it is assumed that the gain adjustment (acoustic aiding process) for each frequency has been completed based on a fitting theory from audiograms of people suffering from hypacusia that were measured in advance. Note that the types of speech sounds to be stored may be the 50 sounds of the 57S list, instead of the 20 speech sounds of the 67S list. The consonant labels are utilized when assessing a consonant that incurs a high annoyance by the user 5.

The reference N1 component latency is a threshold value (in units of ms) for the latency of an N1 component of each speech sound which accounts for the influences of differing characteristic features of speech sound audios. In the case of using standard test audios, the latency of an N1 component that is measured for each speech sound at a sound pressure where a generic user feels annoyance may be used. Without being limited to standard test audios, in the case of using audio recordings of the voice of a person who is a main partner of conversation through the hearing aid, for example, a value which is calculated based on the consonant duration and consonant intensity of each speech sound for presentation may be set, for example. Through a comparison between this reference N1 component latency and the measured N1 component latency, annoyance is judged. The method of annoyance judgment will be described later.

FIG. 15 is again referred to. The presented-speech sound determination section 70 determines which speech sound is to be presented at what sound pressure, by referring to the speech sound DB 71. The speech sounds for presentation may be selected and determined by random order, for example. It is assumed that the sound pressures of the speech sounds for presentation are sound pressures which are obtained after applying an acoustic aiding process to audios of 55 dB SPL, 65 dB SPL, 75 dB SPL, and 85 dB SPL in a speech sound intelligibility curve measurement. The sound pressures may sequentially varied from smaller sound pressures to larger sound pressures, or in the opposite order of this. Alternatively, sound pressures may be selected by random order.

In accordance with the point of audio presentation, the presented-speech sound determination section 70 outputs a trigger to the biological signal measurement section 50, and sends the actual audio to be presented to the event-related potential processing section 55.

The audio output section 11 reproduces the monosyllabic audio which is determined by the presented-speech sound determination section 70, thereby presenting it to the user 5.

The biological signal measurement section 50, which is an electroencephalograph for measuring a biological signal of the user 5, measures an electroencephalogram as the biological signal. Then, the biological signal measurement section 50 subjects the electroencephalogram data to a frequency filtering with a cutoff frequency which is suitable for N1 component extraction, cuts out an event-related potential of the electroencephalogram in a predetermined zone (e.g., a zone from −200 ms to 500 ms) based on the trigger received from the presented-speech sound determination section 70 as a starting point, and sends the waveform data (electroencephalogram data) thereof to the event-related potential processing section 55. The N1 component frequency is about 10 Hz. Therefore, in the case of using a band-pass filter as the frequency filter, it may be set so as to allow a component from 5 Hz to 15 Hz of the electroencephalogram to pass through, for example. It is assumed that the user 5 has already put on the electroencephalograph. The electrode for electroencephalogram measurement is attached at the parietal Pz, for example.

In accordance with the actual audio to be presented that is received from the presented-speech sound determination section 70, the event-related potential processing section 55 performs a summation of the event-related potentials received from the biological signal measurement section 50. The event-related potential processing section 55 may only select the event-related potentials corresponding to audio presentations of the same speech sound, thus performing a summation of the event-related potentials for each speech sound type, for example. Taking a summation only of the event-related potentials for the same speech sound makes possible an annoyance judgment for each speech sound. Since the characteristic features of speech sound audios are similar between speech sounds sharing the same consonant, the summation may be performed for event-related potentials for selected speech sounds that share the same consonant. Alternatively, in FIG. 16, those speech sounds whose differences in reference N1 component latency are within 10 ms may be grouped up for summation. Taking a summation of speech sounds sharing the same consonant enables an annoyance judgment in speech sound listening with respect to each consonant type. Taking a summation of each group of speech sounds whose differences in reference N1 component latency are small enables an annoyance judgment with respect to that group. From a consonant-by-consonant summation, or a group-by-group summation of small differences in reference N1 component latency, a summed waveform is obtained with more than a few summations being made. Moreover, as a characteristic feature of the measured electroencephalogram data, the event-related potential processing section 55 may calculate an S(signal)/N(noise), where the N1 component is the signal, for example. Note that, although an arithmetic mean of event-related potentials is performed in the aforementioned experiment, the mean process is not needed when paying attention to the N1 component latency alone.

The event-related potential processing section 55 sends the electroencephalogram data which has been obtained by performing a summation over a predetermined number of times for each speech sound to the annoyance judgment section 65.

Having received the electroencephalogram data from the event-related potential processing section 55, the annoyance judgment section 65 performs an analysis process described below.

Based on the latency of an N1 component in the electroencephalogram data received from the event-related potential processing section 55, the annoyance judgment section 65 judges whether the user felt annoyed or not. For example, as the N1 component latency, the annoyance judgment section 65 compares a point in time at which a negative potential peak occurs, between 50 ms and 350 ms based on a trigger received from the presented-speech sound determination section 70 as a starting point (hereinafter referred to as a "peak latency"), against the predetermined reference latency (threshold value) which is stored in the speech sound DB 71. Then, if the peak latency of the N1 component is shorter than the predetermined threshold value, an "annoying" judgment is made, and if the peak latency is longer than the predetermined threshold value a "not annoying" judgment is made. As used herein, "annoying" or "being annoyed" means that the speech sound has such a large sound pressure that the user feels uncomfortable. On the other hand, "not annoying" or "not being annoyed" means that the sound pressure of the speech sound is in a range where it is not so loud as to allow the user to feel uncomfortable. Note that, without being limited to a dichotomic judgment of either "annoying" or "not annoying", the annoyance judgment section 65 may determine a difference between the peak latency of the N1 component and the reference latency.

In the case of judging annoyance for each speech sound, for example, a reference latency for each speech sound may be used as the predetermined threshold value. In the case of judging annoyance for each row having the same consonant, a reference latency for each row may be used as the predetermined threshold value. In the case of judging annoyance for each group whose difference in reference latency is small, a reference latency for each group may be used as the predetermined threshold value.

The result accumulating DB 80 receives information of the presented audio from the presented-speech sound determination section 70. Also, the result accumulating DB 80 receives information of the annoyance judgment result for each speech sound from the annoyance judgment section 65. Then, with respect to each speech sound and each sound pressure of the presented audio, for example, the result accumulating DB 80 accumulates information of the received results of annoyance judgment.

Figure 17:
FIG. 17 is a diagram showing an example of accumulated results of annoyance judgment using a technique of Embodiment 1.

FIG. 17 shows an example of data accumulation in the result accumulating DB 80. FIG. 17 illustrates an example where annoyance information is accumulated with respect to each speech sound and each sound pressure. For example, in FIG. 17, "1" denotes a case where the annoyance judgment section 65 determines that the N1 component latency is shorter than the reference latency, thus making an "annoying" judgment, whereas "0" denotes a case where the annoyance judgment section 65 determines that the N1 component latency is longer than the reference latency, thus making a "not annoying" judgment.

Figure 18A:
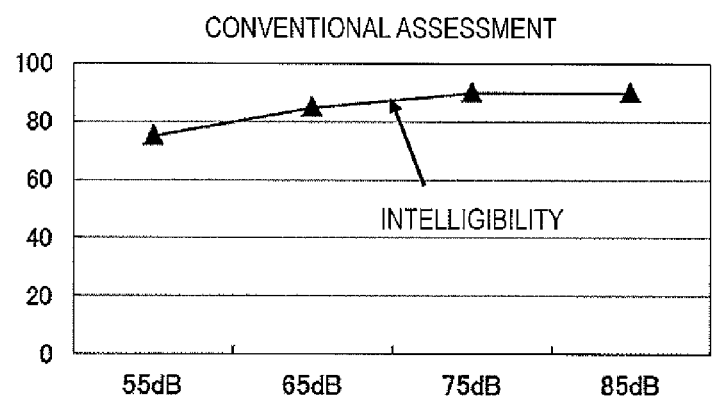
FIG. 18 is diagrams showing results of annoyance judgment using the technique of Embodiment 1, and a conventional speech sound intelligibility curve.
Figure 18B:
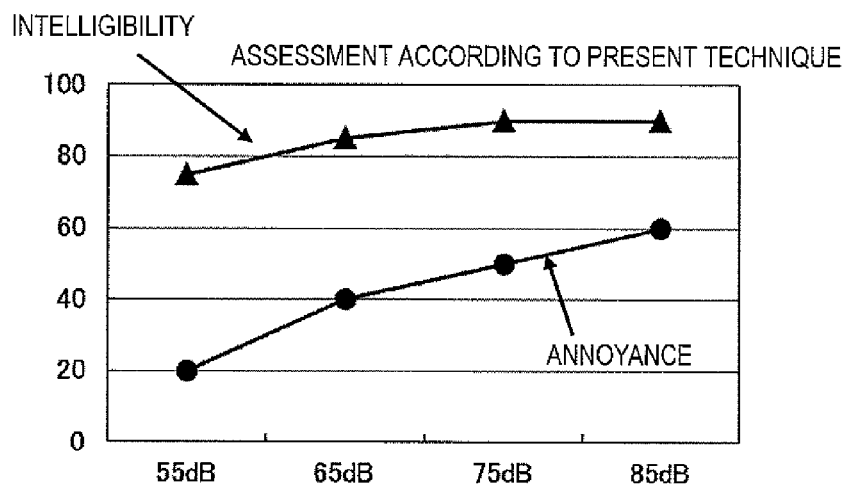
Figure 18C:
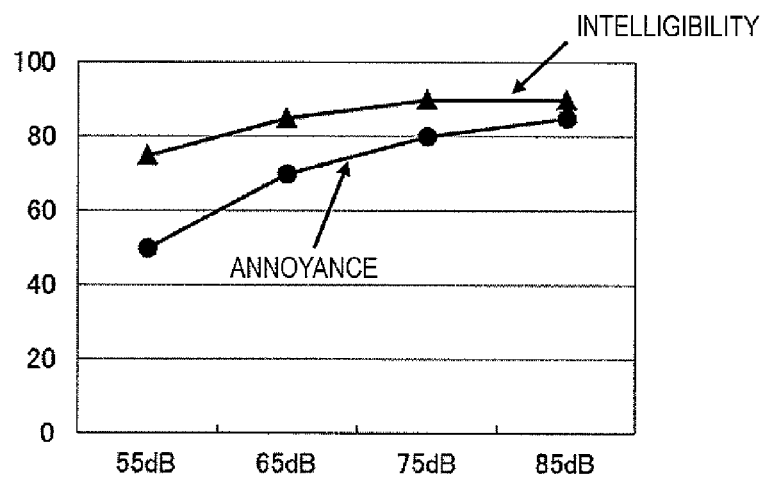

FIGS. 18A to 18C show measurement results of speech sound intelligibility curves (conventional assessment), and in addition to the conventional assessment, exemplary results of an annoyance judgment in speech sound listening according to the present embodiment. FIG. 18A shows an example where only speech sound intelligibility with respect to each sound pressure of the presented audio is assessed when wearing a hearing aid. This example illustrates an assessment result which is obtained by a conventional assessment technique. In this example, the intelligibility is assessed to be 80% or more at a sound pressure of 65 dB SPL or more. Therefore, if the speech sound intelligibility is improved as compared to when not wearing a hearing aid (not shown in FIG. 18), a hearing aid suitability test would determine this case to be suitable.

FIGS. 18B and 18C show exemplary assessment results where annoyance judgment according to the present embodiment is employed in addition to the result of speech sound intelligibility curve measurement when wearing a hearing aid as shown in FIG. 18A. It is assumed that the speech sound intelligibility curve has been separately measured by a conventional method which involves oral explanation, key inputting, or the like.

In FIGS. 18B and 18C, although the intelligibilities are the same, results of annoyance judgment are quite different. For example, in FIG. 18B, the overall assessment of annoyance is low; this leads to an assessment that the user would feel little annoyance with the acoustic aiding process. In FIG. 18C, for example, the overall assessment of annoyance is high, and particularly high at large sound pressures of 65 dB SPL or more; this leads to an assessment that, with this acoustic aiding process, annoyance would be felt at 65 dB SPL, which is the sound pressure of daily conversations. Such assessments permits proposals of specific fitting procedures to be made, e.g., uniformly increasing the amount of gain adjustment in the case of FIG. 18B if the user requests further improvement of intelligibility, or uniformly decreasing the amount of gain adjustment in the case of FIG. 18C and employing enhanced compression in non-linear amplification.

Although FIGS. 18B and 18C illustrate annoyance assessment only when wearing a hearing aid, annoyance may be assessed also when not wearing a hearing aid (naked ear), and an annoyance comparison may be made between when not wearing a hearing aid and when wearing a hearing aid.

Next, with reference to FIG. 19, a processing procedure performed by the annoyance judgment system 100 for speech sound listening of FIG. 15 will be described. FIG. 19 is a flowchart showing a procedure of processing performed by the annoyance judgment system 100 for speech sound listening.

At step S101, by referring to the speech sound DB 71, the presented-speech sound determination section 70 determines a monosyllabic speech sound to be presented and a sound pressure. The audio output section 11 presents the speech sound to the user 5 at the determined sound pressure. The presented-speech sound determination section 70 sends a trigger to the biological signal measurement section 50, and sends audio information concerning the presented speech sound to the event-related potential processing section 55. The speech sound to be presented may be randomly selected from the speech sound DB 71, or a speech sound of a particular consonant or a group may be exclusively selected. The sound pressure of the speech sound for presentation may be, for example, sound pressures which are obtained after applying an acoustic aiding process to audios of 55 dB SPL, 65 dB SPL, 75 dB SPL, and 85 dB SPL in a speech sound intelligibility curve measurement. The sound pressures of presentation may sequentially varied from smaller sound pressures to larger sound pressures, or in the opposite order of this. Alternatively, sound pressures may be selected by random order.

At step S102, upon receiving the trigger from the presented-speech sound determination section 70, the biological signal measurement section 50 cuts out an event-related potential from e.g. −200 ms to 500 ms from the measured electroencephalogram, based on the trigger as a starting point. Then, an average potential from e.g. −200 ms to 0 ms is determined, and the resultant event-related potential is subjected to baseline correction so that this average potential becomes 0 μV.

It is assumed that the biological signal measurement section 50 is always measuring an electroencephalogram during assessment, and applying a frequency filter which is suitable for N1 component extraction to the electroencephalogram data. For example, a suitable frequency filter may be a band-pass filter which allows 5 Hz to 15 Hz, around the center frequency of 10 Hz of the N1 component, to pass. Note that baseline correction is not essential in the case where a high-pass filter of 5 Hz or more is applied to the electroencephalogram data, for example, because there is hardly any influence of changes in the base line at lower frequencies.

At step S103, based on the information of the presented speech sound which is received from the presented-speech sound determination section 70, the event-related potential processing section 55 takes a summation of the event-related potential cut out at step S102 with respect to each speech sound and each sound pressure. Although a summation is performed with respect to each speech sound and each sound pressure level in the present embodiment, it is not necessary that the summation be performed with respect to each speech sound. For example, it may be performed with respect to each speech sound type, e.g., for each consonant or for each group of speech sounds whose difference in reference latency is small, or with respect to each sound pressure level of presentation. In other words, in the case where each speech sound is classified based on at least one of the speech sound type, the consonant type, and the group whose difference in reference latency is small, the event-related potential processing section 55 may take a summation of event-related potentials of electroencephalogram signals which are obtained when speech sounds belonging to the same classification are presented.

At step S104, the event-related potential processing section 55 determines whether the number of summations for the event-related potential with respect to the speech sound presented at step S101 has reached a predetermined number of summations or not. If the number of summations is less than the predetermined number of times, the process returns to step S101 to repeat audio presentation. If the number of summations is equal to or greater than the predetermined number of times, the process proceeds to step S105. The predetermined number be 20 times, for example. Note that "20 times" is a mere example, although it is a number of summations which is frequently adopted in fields where event-related potentials are to be measured. For example, the event-related potential processing section 55 may calculate an S(signal)/N(noise), where the N1 component is the signal, and a number of summations beyond which the S/N attains a certain level or more may be chosen as the predetermined number of times.

At step S105, the event-related potential processing section 55 sends the electroencephalogram data obtained by taking a summation over a predetermined number of times to the annoyance judgment section 65.

At step S106, the annoyance judgment section 65 determines the N1 component latency of the electroencephalogram data received from the event-related potential processing section 55, and compares it against the reference N1 component latency received from the speech sound DB 71. The N1 component latency of the electroencephalogram data may be a point in time at which the potential becomes smallest, within a zone from 0 ms to 500 ms, for example. In the case where a summation with respect to each speech sound and each sound pressure has been performed at step S103, a comparison between the reference latency for each speech sound and the N1 component latency of the electroencephalogram data is made.

At step S107, if the N1 component latency of the electroencephalogram data is shorter than the reference latency, the annoyance judgment section 65 judges that the user 5 has felt annoyed. On the other hand, if the N1 component latency of the electroencephalogram data is longer than the reference latency, the annoyance judgment section 65 judges that the user 5 has felt not annoyed.

At step S108, the result accumulating DB 80 accumulates information of the annoyance judgment result received from the annoyance judgment section 65, with respect to each speech sound and each sound pressure presented at step S101.

At step S109, the presented-speech sound determination section 70 determines whether stimulation presentation has been completed for all of the speech sounds and sound pressures to be subjected to an assessment of annoyance in speech sound listening. If it is not completed, the process returns to step S101; if it is completed, the annoyance judgment in speech sound listening is ended.

From the results of annoyance judgment which are accumulated in the result accumulating DB 80 with respect to each speech sound and each sound pressure, proposals of more specific fitting procedures can be made. For example, if a result of speech sound intelligibility curve measurement as shown in FIG. 18B is obtained, where the overall assessment of annoyance is considered to be low, the amount of gain adjustment may be uniformly increased if the user requests further improvement in intelligibility. As a result, a fitting which is more appropriate for that user can be realized. On the other hand, if a result of speech sound intelligibility curve measurement as shown in FIG. 18C is obtained, a fitting may be proposed which involves uniformly decreasing the amount of gain adjustment and further employing enhanced compression in non-linear amplification.

In the present embodiment, on the premise of presenting a monosyllabic speech sound in the form of an audio, annoyance in speech sound listening is assessed through a process which utilizes a negative component at a latency of about 200 ms, of an event-related potential based on the point of audio presentation as a starting point. Through the above process, in speech sound listening, a judgment can be made as to how annoyed the user was (annoyance). This means that suitability of an acoustic aiding process can be assessed from the perspective of annoyance in speech sound listening, which is distinct from speech sound intelligibility. Since acoustic aiding process assessments are possible from the perspective of annoyance, an acoustic aiding process which does not cause the user to feel annoyed in speech sound listening and which does not induce aural fatigue can be realized.

Note that, as shown in FIG. 14, the annoyance judgment apparatus 1 for speech sound listening in the present embodiment is realized with a construction which permits downsizing and which employs generic hardware. By constructing the annoyance judgment apparatus 1 in a portable size and weight that allows the user to carry it with himself or herself, it becomes possible to assess a comfortableness of speech sound listening in an acoustic environment in which the user actually uses a hearing aid. Although the audio output section 11 is illustrated as a speaker set in FIG. 13, the audio output section 11 may instead be headphones. Use of headphones facilitates transportation, thus enabling an assessment of speech sound listening in an environment in which the user uses them.

The present embodiment has been illustrated based on assessments for the Japanese language. However, it may be English or Chinese so long as the speech sounds are monosyllabic. In the case of English, for example, monosyllabic words may be presented, and an evaluation may be made on a word-by-word basis. A monosyllabic English word is an audio spanning a short period of time, and is composed of a consonant(s) and a vowel. Therefore, basically similarly to the aforementioned Japanese monosyllabic speech sounds, a reference latency can be determined for each word based on consonant duration and consonant intensity.

FIG. 20 shows an exemplary result of assessing annoyance for different monosyllabic words. In FIG. 20, "1" indicates that the user felt annoyed, whereas "0" indicates that the user did not feel annoyed.

According to the annoyance judgment system 100 for speech sound listening of the present embodiment, as a user merely hears an audio, a judgment can be made as to how annoyed he or she was in speech sound listening (annoyance). As a result, an "annoyance" in speech sound listening that is felt by the user can be quantified, whereby an assessment of an acoustic aiding process can be made from the perspective of annoyance, thus permitting a fitting not inducing annoyance and aural fatigue.

In the description of the present embodiment, the biological signal measurement section 50 is illustrated as cutting out an event-related potential in a predetermined range based on a trigger from the presented-speech sound determination section 70 as a starting point, subjecting it to a baseline correction, and sending potential waveform data to the event-related potential processing section 55. However, this process is an example. As another process, for example, the biological signal measurement section 50 may constantly measure an electroencephalogram, cut out an event-related potential as needed by the event-related potential processing section 55, and subject it to a baseline correction. With such a construction, the presented-speech sound determination section 70 does not need to send a trigger to the biological signal measurement section 50, and may only send a trigger to the event-related potential processing section 55.

Although the present embodiment illustrates that the annoyance judgment results are accumulated in the result accumulating DB 80, accumulation is not necessary. For example, in the case where the result accumulating DB 80 is provided external to the annoyance judgment apparatus 1, the annoyance judgment section 65 may simply output the result of judgment. The result of judgment can be utilized as information concerning annoyance in speech sound listening.

The annoyance judgment system illustrated in the present embodiment makes a judgment as to how annoying a speech sound was felt to be (annoyance), based on the latency of a negative component around 200 ms (more specifically, from 50 ms to 350 ms) in the user electroencephalogram after audio presentation. By setting a different reference latency for each speech sound, a highly precise annoyance assessment is enabled irrespective of characteristic features such as the duration of the consonant portion (consonant duration) and the intensity of the consonant portion (consonant intensity) of each speech sound. Through annoyance judgment in speech sound listening, an acoustic aiding process can be selected which does not allow the user to feel annoyance and which is not likely to induce fatigue even if a hearing aid is worn for a long period of time.

Embodiment 2

In the annoyance judgment system 100 for speech sound listening of Embodiment 1, according to one type of acoustic aiding process stored in the speech sound DB 71, annoyance in speech sound listening is judged for predetermined audios that have been previously adjusted, based on the latency of an N1 component.

However, due to increasing precision in the signal processing of the recent years, acoustic aiding processing methods for realizing functions such as consonant emphasis, directivity, and noise reduction are under development. This imposes a limitation on searching for and identifying an optimum acoustic aiding process based on the annoyance judgment results for a single acoustic aiding process alone.

Therefore, the present embodiment will illustrate an annoyance judgment system for speech sound listening including an acoustic aiding processing section which modifies presented speech sounds into sounds to be output through a hearing aid, and assesses annoyance for each one of different acoustic aiding processes.

Figure 21:
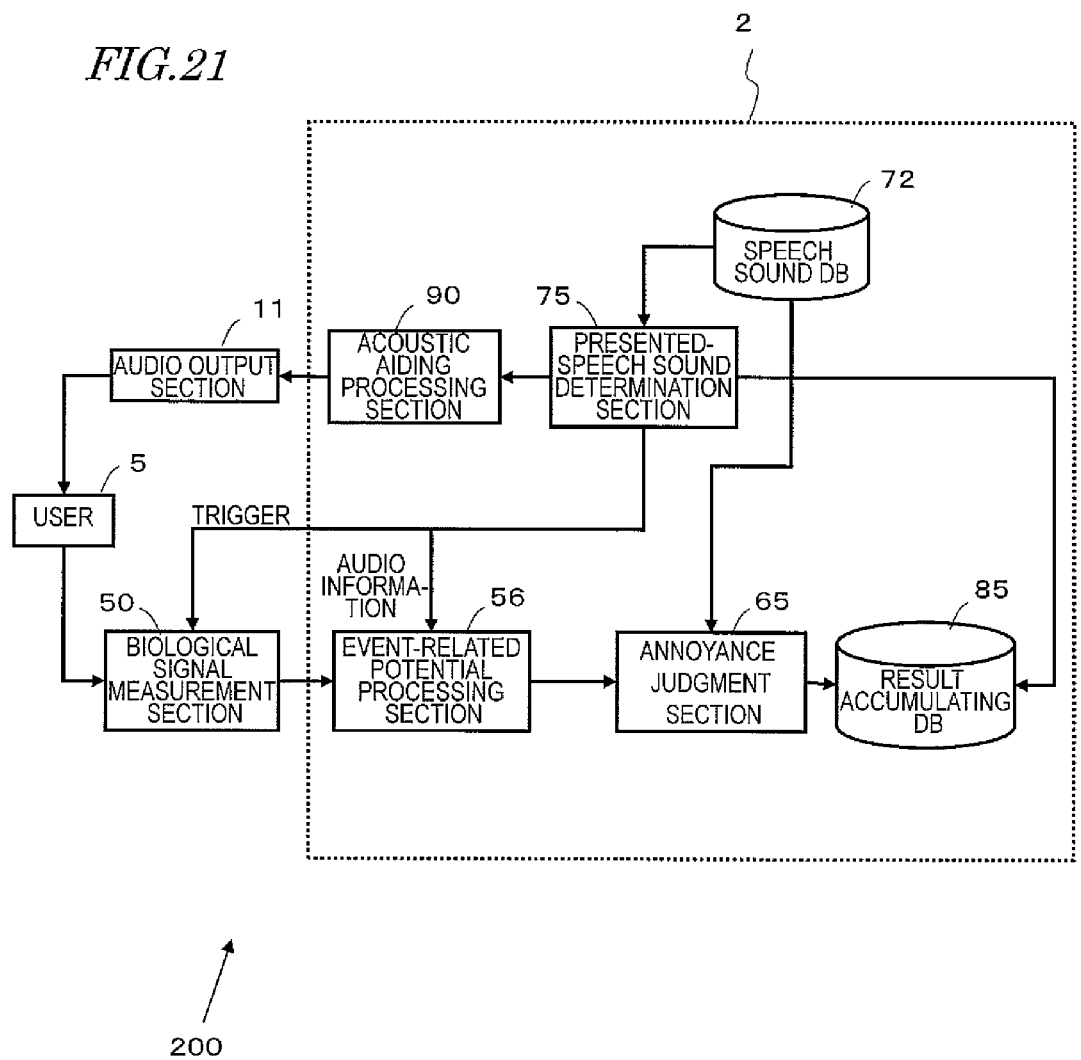
FIG. 21 is a diagram showing the functional block construction of an annoyance judgment system 200 for speech sound listening according to Embodiment 2.

FIG. 21 shows a functional block construction of an annoyance judgment system 200 for speech sound listening of the present embodiment. The annoyance judgment system 200 for speech sound listening includes an audio output section 11, a biological signal measurement section 50, and an annoyance judgment apparatus 2 for speech sound listening. Any block which has an identical counterpart in FIG. 15 is denoted by a like reference numeral, and the description thereof is omitted. The hardware construction of the annoyance judgment apparatus 2 for speech sound listening is as shown in FIG. 14. The annoyance judgment apparatus 2 for speech sound listening of the present embodiment shown in FIG. 21 is realized as a program which defines a different process from that of the program 35 described in Embodiment 1 (FIG. 14) is executed. The annoyance judgment system 200 may also be referred to as an acoustic aiding processing system.

One large difference of the annoyance judgment apparatus 2 for speech sound listening of the present embodiment from the annoyance judgment apparatus 1 for speech sound listening of Embodiment 1 is that an acoustic aiding processing section 90 is additionally introduced. Although each component element of the annoyance judgment apparatus 2 is basically given the same name as that used in Embodiment 1, they may be denoted by different reference numerals when having different operations and/or functions. For example, the present embodiment performs an annoyance judgment for each of a plurality of acoustic aiding processes, which is not performed in Embodiment 1; therefore, in the place of the event-related potential processing section 55, the presented-speech sound determination section 70, the speech sound DB 71, and the result accumulating DB 80 of Embodiment 1, the present embodiment employs an event-related potential processing section 56, a presented-speech sound determination section 75, a speech sound DB 72, and a result accumulating DB 85.

Hereinafter, the speech sound DB 72, the presented-speech sound determination section 75, the acoustic aiding processing section 90, the event-related potential processing section 56, the result accumulating DB 85, and the acoustic aiding processing section 90 will be described.

Similarly to the speech sound DB 71 of Embodiment 1, the speech sound DB 72 is a speech sound database with which to conduct an annoyance judgment in speech sound listening, as in the 20 speech sounds of the 67S list shown in FIG. 16, for example. Similarly to the speech sound DB 71, the speech sound DB 72 also retains information of a reference N1 component latency for each speech sound. The speech sound DB 72 differs from the speech sound DB 71 in that the speech sound DB 72 contains speech sound data before being subjected to an acoustic aiding process.

Similarly to the presented-speech sound determination section 70 of Embodiment 1, the presented-speech sound determination section 75 determines a speech sound type and a sound pressure by referring to the speech sound DB. The presented-speech sound determination section differs from the presented-speech sound determination section 70 in that the presented-speech sound determination section 75 allows a selection as to which acoustic aiding process an audio is to be modified through, and it sends also the audio data of the speech sound for presentation to the acoustic aiding processing section 90.

Based on the instruction concerning the acoustic aiding process to be selected and the audio data received from the presented-speech sound determination section 75, the acoustic aiding processing section 90 modifies the audio data with the designated acoustic aiding processing method. The acoustic aiding process may involve consonant emphasis, directivity, noise reduction, etc., for example. In the case where an acoustic aiding process involving consonant emphasis is selected, for example, a process of increasing the amount of gain amplification for consonant frequencies than usual is performed, thus modifying the audio data. Note that the acoustic aiding processing section 90 may rely on the judgment result by the annoyance judgment section 65 to adjust the amount of gain amplification for audios. For example, for the audio data of a speech sound that is judged as annoying by the annoyance judgment section 65, the amount of gain amplification is reduced. For the audio data of a speech sound judged as not annoying by the annoyance judgment section 65, the amount of gain amplification is not adjusted. Alternatively, the amount of gain amplification may be determined on the basis of a difference between the peak latency of the N1 component and the reference latency as determined by the annoyance judgment section 65. For example, if the difference between the peak latency of the N1 component and the reference latency is within a predetermined range, the acoustic aiding processing section 90 does not adjust the amount of gain amplification. As the difference between the peak latency of the N1 component and the reference latency deviates away from the upper limit value or lower limit value of the predetermined range, the acoustic aiding processing section 90 decreases the amount of gain amplification.

Similarly to the event-related potential processing section 55 of Embodiment 1, in accordance with the actual audio to be presented which is received from the presented-speech sound determination section 75, the event-related potential processing section 56 performs a summation for the event-related potentials received from the biological signal measurement section 50. A difference between the event-related potential processing section 56 and the event-related potential processing section 55 is that, upon receiving the information of an acoustic aiding process from the presented-speech sound determination section 75, the event-related potential processing section 56 performs a summation with respect to each speech sound, each sound pressure, and each acoustic aiding process.

Similarly to the result accumulating DB 80 of Embodiment 1, the result accumulating DB 85 accumulates information of annoyance judgment results (based on N1 component latency) received from the annoyance judgment section 65, e.g., with respect to each speech sound and each sound pressure. A difference between the result accumulating DB 85 and the result accumulating DB 80 is that, from the presented-speech sound determination section 75, the result accumulating DB 85 receives not only information of the speech sound and sound pressure of the presented stimulation, but also information of an acoustic aiding process type, and accumulates the data with respect to each acoustic aiding process type.

FIGS. 22A and 22B show examples of data accumulation in the result accumulating DB 85. FIGS. 22A and 22B illustrate examples where the results of annoyance judgment are accumulated with respect to each speech sound, each sound pressure, and each acoustic aiding process. FIG. 22A shows a pattern under acoustic aiding process A, whereas FIG. 22B shows a pattern under acoustic aiding process B. Each indicates annoyance assessment results in the case where speech sounds are subjected to the respective acoustic aiding process. In FIGS. 22A and 22B, "1" indicates the case where the annoyance judgment section 65 judges that the N1 component latency is shorter than the reference latency and that the user 5 has felt annoyed, and "0" indicates the case where the annoyance judgment section 65 judges that the N1 component latency is longer than the reference latency and that the user 5 has not felt annoyed. From a comparison between FIGS. 22A and 22B, it can be said that there are fewer "1's" (i.e., the user is feeling less annoyance) in FIG. 22B where an acoustic aiding process is performed based on the pattern of acoustic aiding process B.

Next, with reference to FIG. 23, an overall procedure of processing that is performed in the annoyance judgment system 200 for speech sound listening will be described.

Figure 23:
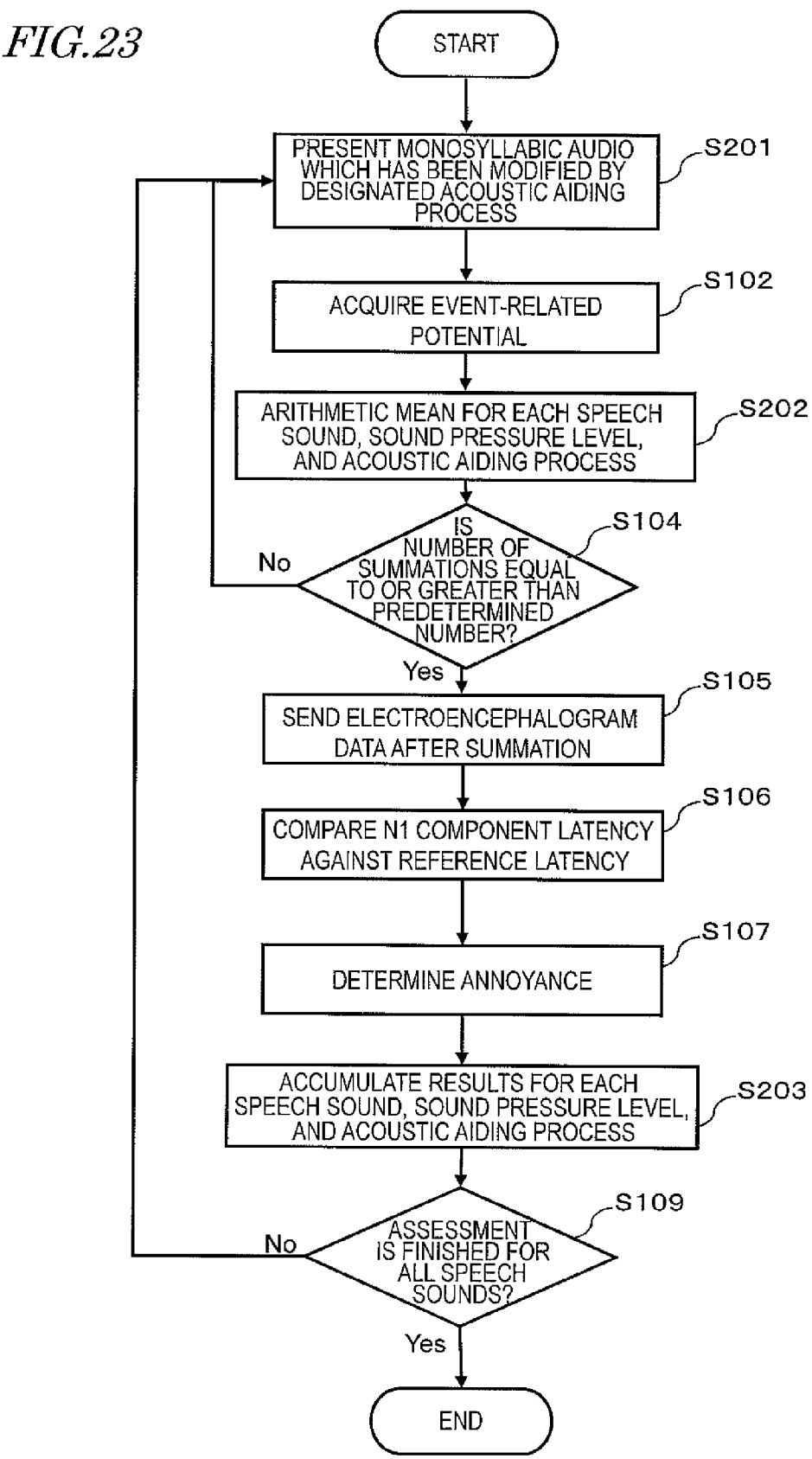
FIG. 23 is a flowchart showing a processing procedure of the annoyance judgment system 200 for speech sound listening according to Embodiment 2.

FIG. 23 is a flowchart showing the processing procedure by the annoyance judgment system 200 for speech sound listening of the present embodiment. In FIG. 23, any step where a process identical to a process by the annoyance judgment system 100 for speech sound listening (FIG. 19) will be denoted by a like reference numeral, and the description thereof will be omitted.

The processes by the annoyance judgment system 200 for speech sound listening of the present embodiment differ from the processes by the annoyance judgment system 100 for speech sound listening of Embodiment 1 in steps S201, S202, and S203. At step S201, a monosyllabic audio which is modified through the designated acoustic aiding process is presented. At step S202, a summation is performed with respect to each speech sound, each sound pressure, and each acoustic aiding process. At step S203, results are accumulated with respect to each speech sound, each audio, and each acoustic aiding process. Any other steps have already been described in connection with FIG. 19, and the descriptions thereof are omitted.

At step S201, the presented-speech sound determination section 75 determines the type and sound pressure of the audio to be presented by referring to the speech sound DB 72, and acquires the data thereof. Furthermore, the presented-speech sound determination section determines an acoustic aiding process, and sends the information concerning the acoustic aiding process type and the audio data to the acoustic aiding processing section 90. The acoustic aiding processing section 90 determines the information concerning the acoustic aiding process type as determined by the presented-speech sound determination section 75 and the audio data, and modifies the audio data based on the designated acoustic aiding processing method. The audio output section 11 presents the modified audio data to the user 5.

At step S202, information of the type of speech sound for presentation, sound pressure, and acoustic aiding process received from the presented-speech sound determination section 75, the event-related potential processing section 56 takes a summation of the event-related potential of the electroencephalogram measured by the biological signal measurement section 50, e.g., with respect to each speech sound, each sound pressure, and each acoustic aiding process.

At step S203, with respect to each of the pieces of information concerning the speech sound for presentation (speech sound type, sound pressure, acoustic aiding process) received from the presented-speech sound determination section 75, the result accumulating DB accumulates the result of annoyance judgment based on the N1 component latency as determined by the annoyance judgment section 65. Examples of accumulated results are as shown in FIG. 22.

Through such processes, comfortableness in speech sound listening can be assessed, e.g., with respect to each acoustic aiding process such as consonant emphasis, directivity, or noise reduction.

Although the present embodiment contemplates a case where audios having been subjected to a plurality of types of acoustic aiding processes are mixed up and presented in random order, annoyance judgment may be performed in sequential order among different types of acoustic aiding processes, e.g., acoustic aiding process A first and then acoustic aiding process B, for example. Performing annoyance judgment for each different type of acoustic aiding process provides an advantage in that the parameters in the subsequently following acoustic aiding process can be changed in accordance with the result of annoyance judgment.

With the annoyance judgment system 200 for speech sound listening of the present embodiment, annoyance for each acoustic aiding process can be assessed. As a result, selection of an acoustic aiding process which is adapted to the purpose of wearing a hearing aid and to the environment of use can be realized.

Embodiment 3

In the annoyance judgment system 100 for speech sound listening of Embodiment 1, the annoyance judgment section 65 makes an annoyance judgment through comparison between a reference N1 component latency of a generic user for each speech sound and the latency of an N1 component of the measured electroencephalogram data.

The N1 component is an incipient component of an event-related potential called the evoked potential, and is believed to have relatively small individual differences concerning latency/amplitude. However, it is not that the N1 component is completely free of latency/amplitude individual differences. Therefore, there has been a limit to making a high precision annoyance judgment through identification based on a reference latency which is obtained from the latency of an N1 component of a generic user for each speech sound.

Accordingly, in the present embodiment, prior to annoyance judgment in speech sound listening, a calibration is made for measuring the reference N1 component latency of each user, and annoyance is assessed based on the N1 component traits of each individual. As a result, in the present embodiment, annoyance judgment can be made with a higher precision than in Embodiment 1.

Figure 24:
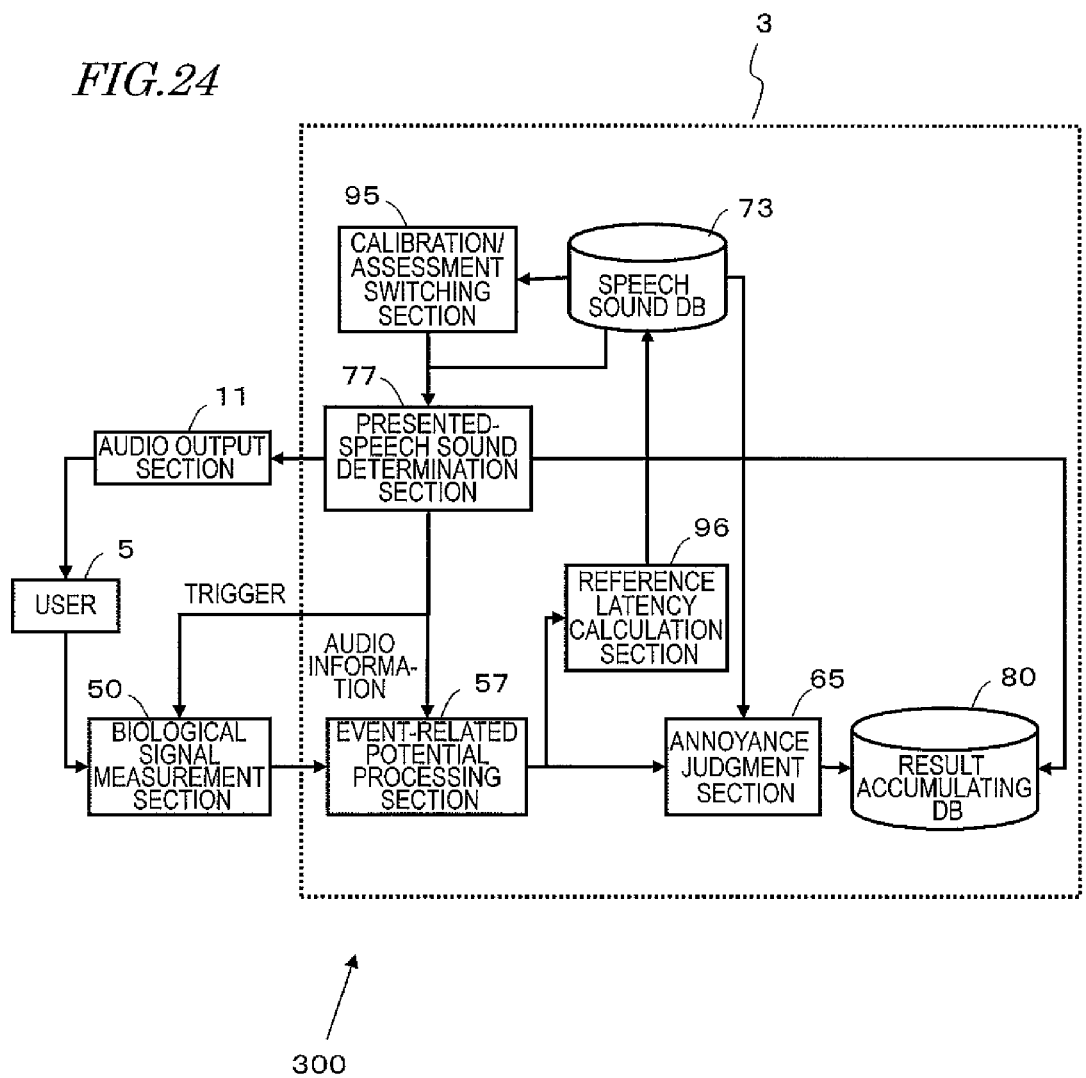
FIG. 24 is a diagram showing the functional block construction of an annoyance judgment system 300 for speech sound listening according to Embodiment 3.

FIG. 24 shows a functional block construction of an annoyance judgment system 300 for speech sound listening of the present embodiment. The annoyance judgment system 300 for speech sound listening includes an audio output section 11, a biological signal measurement section 50, and an annoyance judgment apparatus 3 for speech sound listening. Any block which has an identical counterpart in FIG. 15 is denoted by a like reference numeral, and the description thereof is omitted. The hardware construction of the annoyance judgment apparatus 3 for speech sound listening is as shown in FIG. 14. The annoyance judgment apparatus 3 for speech sound listening of the present embodiment shown in FIG. 24 is realized as a program which defines a different process from that of the program 35 described in Embodiment 1 (FIG. 14) is executed.

One large difference of the annoyance judgment apparatus 3 for speech sound listening of the present embodiment from the annoyance judgment apparatus 1 for speech sound listening of Embodiment 1 is that a calibration/assessment switching section 95 and a reference latency calculation section 96 are additionally introduced. Moreover, a reference N1 component latency of each user is obtained for each speech sound, and in order to perform annoyance judgment based on this reference latency, the present embodiment employs a presented-speech sound determination section 77, an event-related potential processing section 57, and a speech sound DB 73, in the place of the presented-speech sound determination section 70, the event-related potential processing section 55, and the speech sound DB 71 (FIG. 15) of Embodiment 1.

Hereinafter, the calibration/assessment switching section 95, the reference latency calculation section 96, the presented-speech sound determination section 77, the event-related potential processing section 57, and the speech sound DB 73 will be described.

The calibration/assessment switching section 95 switches between a calibration mode for identifying a reference N1 component latency of each user for each speech sound, and an assessment mode of making an annoyance judgment based on the identified reference latency and a measured N1 component latency. Then, calibration/assessment switching section 95 sends information representing the current mode to the presented-speech sound determination section 77. Note that the mode switching may be conducted at a point in time when a reference latency for each speech sound is written to the speech sound DB 73, or when a predetermined number of times of speech sound presentation that is required for identifying the reference N1 component latency of the user electroencephalogram for each speech sound are finished.

The presented-speech sound determination section 77 refers to the speech sound DB 73 to determine a speech sound type and the sound pressure of the presented audio, and outputs the speech sound to the user 5 via the audio output section 11, and also sends trigger information to the biological signal measurement section 50. Moreover, the presented-speech sound determination section 77 receives calibration mode/assessment mode information from the calibration/assessment switching section 95, and sends audio information and the calibration/assessment mode information to the event-related potential processing section 57. The presented-speech sound determination section 77 switches its operation in accordance with the mode received from the calibration/assessment switching section 95. In the calibration mode, an audio of a vowel (a monosyllabic sound with no consonant portion) may be presented as a predetermined sound pressure, for example. By presenting a vowel as the speech sound audio, the N1 component latency to serve as a basis for each user can be identified without the influence of a consonant portion. The predetermined sound pressure is a sound pressure which is above a threshold value at which the user can hear an audio. For example, it may be a sound pressure which is felt as "annoying" by the user. The sound pressure above which the user is able to hear and the sound pressure at which the user feels annoyed may be determined based on the user's audiogram, or previously measured through subjective evaluation, for example. In the assessment mode, the presented-speech sound determination section 77 presents a speech sound at a predetermined sound pressure, similarly to the presented-speech sound determination section 70.

Similarly to the event-related potential processing section 55, the event-related potential processing section 57 takes a summation of the event-related potentials received from the biological signal measurement section 50, in accordance with the actual audio to be presented which is received from the presented-speech sound determination section 77. Moreover, the event-related potential processing section 57 switches its operation in accordance with mode information received from the presented-speech sound determination section 77. In the calibration mode, a summation is taken with respect to each vowel, for example, and after a predetermined number of times of summation are finished, the summed waveform with respect to each vowel is sent to the reference latency calculation section 96. In the assessment mode, similarly to the event-related potential processing section 55, a summed waveform with respect to each speech sound and each sound pressure is sent to the annoyance judgment section 65.

Receiving the summed waveform data with respect to each vowel from the event-related potential processing section 57, the reference latency calculation section 96 determines the latency of an N1 component. The N1 component latency may be a point in time at which the potential becomes smallest within a range from 50 ms to 350 ms, for example. For example, if the presented-speech sound determination section 77 has set a sound pressure which is felt as "annoying" by the user as the sound pressure, the N1 component latency determined with respect to each vowel is regarded as the reference latency for the respective vowel. By measuring an N1 component latency for the vowel, it becomes possible to determine a reference N1 component latency for each vowel in accordance with the differing sound characteristic features of different vowels. The reference latency for any speech sound containing a consonant portion is obtained by adding a predetermined positive value, which is adapted to the characteristic feature of the consonant portion, to the reference latency for each vowel. The predetermined positive value is determined for each consonant. For example, in the case of a speech sound whose consonant portion has a weak intensity, the consonant duration may be used as the predetermined positive value. In the case of a speech sound whose consonant portion has a strong intensity, for example, the time which elapses until the intensity of the consonant portion becomes equal to or greater than a predetermined value may be used as the predetermined positive value. Then, the calculated result is written to the speech sound DB 73.

As compared to consonants, differences in audio characteristic features from speech sound to speech sound are smaller among vowels. Therefore, a mean of N1 component latencies for all vowels may be taken, which may be used as a reference N1 component latency for vowels. Alternatively, only a mean of the latencies for those vowels which permitted stable measurement of an N1 component may be taken, and this may be used as a reference N1 component latency for vowels.

The speech sound DB 73 is a database of speech sounds for use in the annoyance judgment in speech sound listening, similarly to the speech sound DB 71 exemplified in FIG. 16. A difference between the speech sound DB 73 and the speech sound DB 71 is that the speech sound DB 73 permits rewrite of reference N1 component latencies. Until the reference latency calculation section 96 rewrites the reference N1 component latency, indicating that no reference latency has been set may be retained for each speech sound.

Next, with reference to the flowchart of FIG. 25, an overall procedure of processing performed by the annoyance judgment system 300 for speech sound listening will be described.

Figure 25:
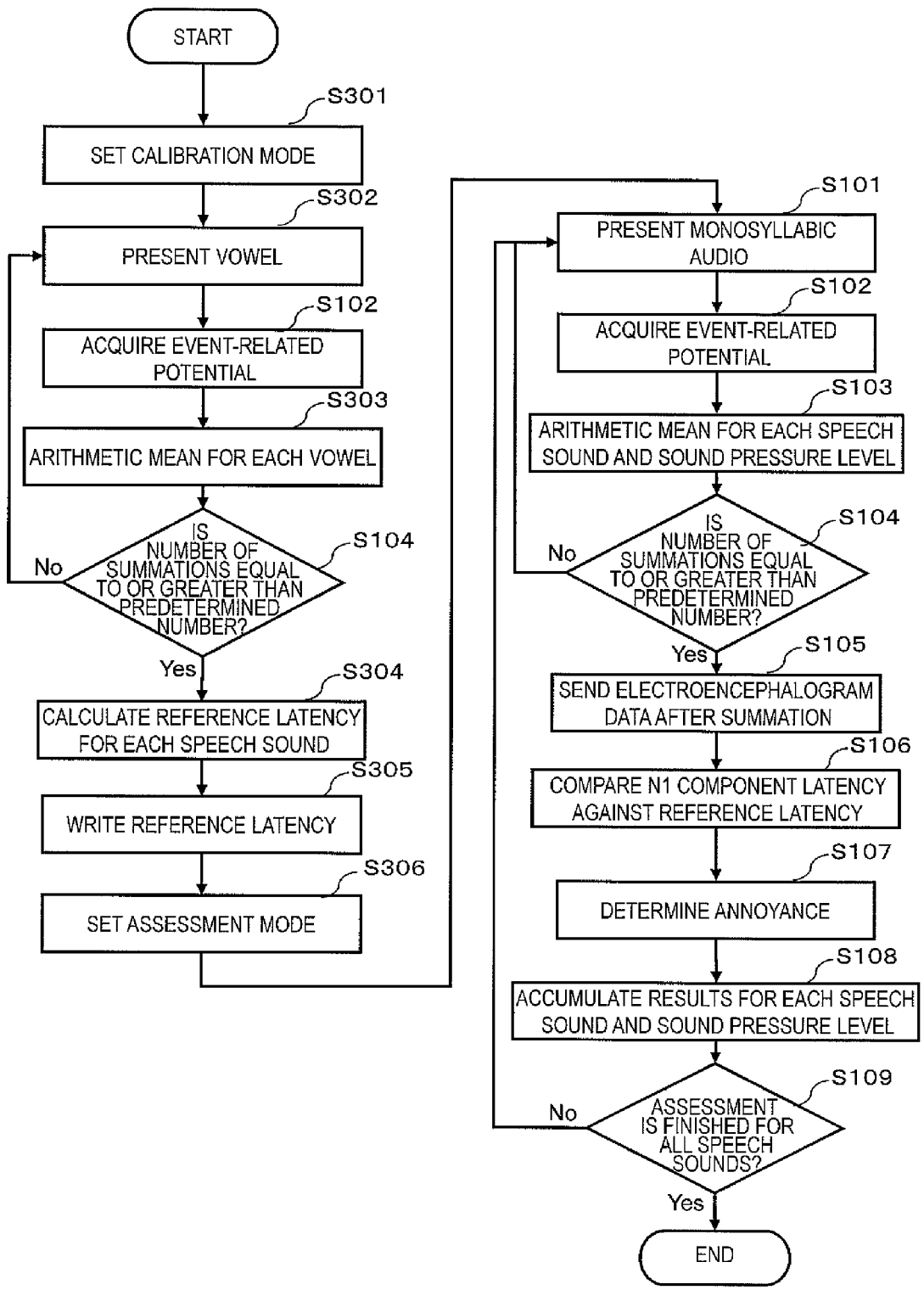
FIG. 25 is a flowchart showing a processing procedure of the annoyance judgment system 300 for speech sound listening according to Embodiment 3.

FIG. 25 is a flowchart showing the processing procedure by the annoyance judgment system 300 of the present embodiment. In FIG. 25, any step where a process identical to a process by the annoyance judgment system 100 for speech sound listening (FIG. 19) will be denoted by a like reference numeral, and the description thereof will be omitted.

The processes by the annoyance judgment system 300 for speech sound listening of the present embodiment differ from the processes by the annoyance judgment system 100 for speech sound listening of Embodiment 1 in steps S301 to S306. Any other steps have already been described in connection with FIG. 19, and the descriptions thereof are omitted.

At step S301, the calibration/assessment switching section 95 sets the current mode to the calibration mode, and sends information indicating the calibration mode to the presented-speech sound determination section 77. The calibration/assessment switching section 95 may refer to the speech sound DB 73, and if the value of the reference N1 component latency is 0, select the calibration mode. Moreover, the calibration mode may be allowed to stand until a predetermined number of times audio presentation are finished. Note that the switching between the calibration and assessment modes may be performed by a hearing aid fitting expert or be based on selections by the user 5.

At step S302, the presented-speech sound determination section 77 refers to the speech sound DB 73 to select a vowel, for example, and outputs it at a predetermined sound pressure to the user 5 via the audio output section 11. The predetermined sound pressure is a sound pressure which is above a threshold value at which the user can hear an audio. For example, it may be a sound pressure which is felt as "annoying" by the user. The sound pressure above which the user is able to hear and the sound pressure at which the user feels annoyed may be determined based on the user's audiogram.

At step S303, the event-related potential processing section 57 takes a summation of the event-related potential measured by the biological signal measurement section 50 with respect to each vowel.

At step S304, from the event-related potential processing section 57, the reference latency calculation section 96 receives waveform data after vowel-for-vowel summation, and determines the latency of an N1 component. The N1 component latency may be a point in time at which the potential becomes smallest within a range from 50 ms to 350 ms, for example. For example, if the presented-speech sound determination section 77 has set a sound pressure which is felt as "annoying" by the user as the sound pressure, the N1 component latency determined with respect to each vowel is regarded as the reference latency for the respective vowel. The reference latency for any speech sound containing a consonant portion is obtained by adding a predetermined positive value, which is adapted to the characteristic feature of the consonant portion, to the reference latency for each vowel. The predetermined positive value is determined for each consonant. For example, in the case of a speech sound whose consonant portion has a weak intensity, the consonant duration may be used as the predetermined positive value. In the case of a speech sound whose consonant portion has a strong intensity, for example, the time which elapses until the intensity of the consonant portion becomes equal to or greater than a predetermined value may be used as the predetermined positive value.

At step S305, the reference latency calculation section 96 writes the reference N1 component latency for each speech sound calculated at step S304 to the speech sound DB 73.

At step S306, upon detecting that a reference N1 component latency has been written to the speech sound DB 73, the calibration/assessment switching section 95 switches from the calibration mode to the assessment mode, and sends information indicating the assessment mode to the presented-speech sound determination section 77. The mode switching may occur when a predetermined number of times of audio presentation are finished, or be made based on a control input by a hearing aid fitting expert or the user 5.

Through such processes, it becomes possible compare the reference N1 component latency of each user for each speech sound and the latency of an N1 component of the measured electroencephalogram data, whereby annoyance in speech sound listening can be assessed with a higher precision.

In the present embodiment, a vowel(s) is selected by the presented-speech sound determination section 77 in the calibration mode, and a reference latency for the vowel(s) is determined based on an N1 component latency(s) for the vowel(s), from which reference latencies for consonants are calculated. By doing so, it becomes unnecessary to calculate reference latencies for all speech sounds, whereby a test can be conducted in a short period of time. However, this is only an example. For example, all speech sounds to be subjected to annoyance judgment may be presented in the calibration mode, and reference latencies may be determined for all of the speech sounds. Alternatively, for example, pure tones which are generally measured in audiograms, e.g., 250 Hz, 500 Hz, 1 kHz, 2 kHz, and 4 kHz may be retained in the presented-speech sound determination section 77, and these pure tones may be presented in the calibration mode, and a reference latency for each speech sound may be calculated from the N1 component latencies for the pure tones.

With the annoyance judgment system 300 for speech sound listening of the present embodiment, annoyance can be highly accurately assessed in accordance with the electroencephalographic traits of each user. As a result, an acoustic aiding process which does not induce annoyance and aural fatigue in the user can be realized.

Although Embodiments 1 to 3 above illustrate that the speech sound DB is provided in the annoyance judgment apparatus for speech sound listening, this is not a requirement. The speech sound. DB may be provided in a database server (not shown) or an external storage device which is connected to the annoyance judgment apparatus for speech sound listening via a network, for example. In that case, the annoyance judgment system for speech sound listening of each embodiment includes the database server or external storage device.

Embodiment 4

In the annoyance judgment system 100 for speech sound listening of Embodiment 1, speech sound DB 71 recorded audios and reference N1 component latencies for speech sounds, each of which is adapted to the characteristic feature of the respective speech sound audio, are retained, and an annoyance judgment is made through a comparison of the latency of an N1 component of the measured electroencephalogram data. The recorded audios may be standard test audios or audios from a person who is a main partner of conversation through the hearing aid (hereinafter referred to as "speaker A"), for example. Annoyance determination for audios which are utterances of speaker A pertains to an assessment of audios with which speaker A speaks to the user in daily life, and is important.

However, recording audios of speaker A prior to annoyance judgment is troublesome to both speaker A and a hearing aid fitting expert.

Therefore, in the present embodiment, speech sound audios uttered by speaker A are analyzed in real time; a reference N1 component latency of the user 5 is estimated in accordance with the characteristic feature of the speech sound audios of speaker A, and annoyance is assessed through comparison between the estimated reference latency and an N1 component latency of the measured electroencephalogram.

Figure 26:
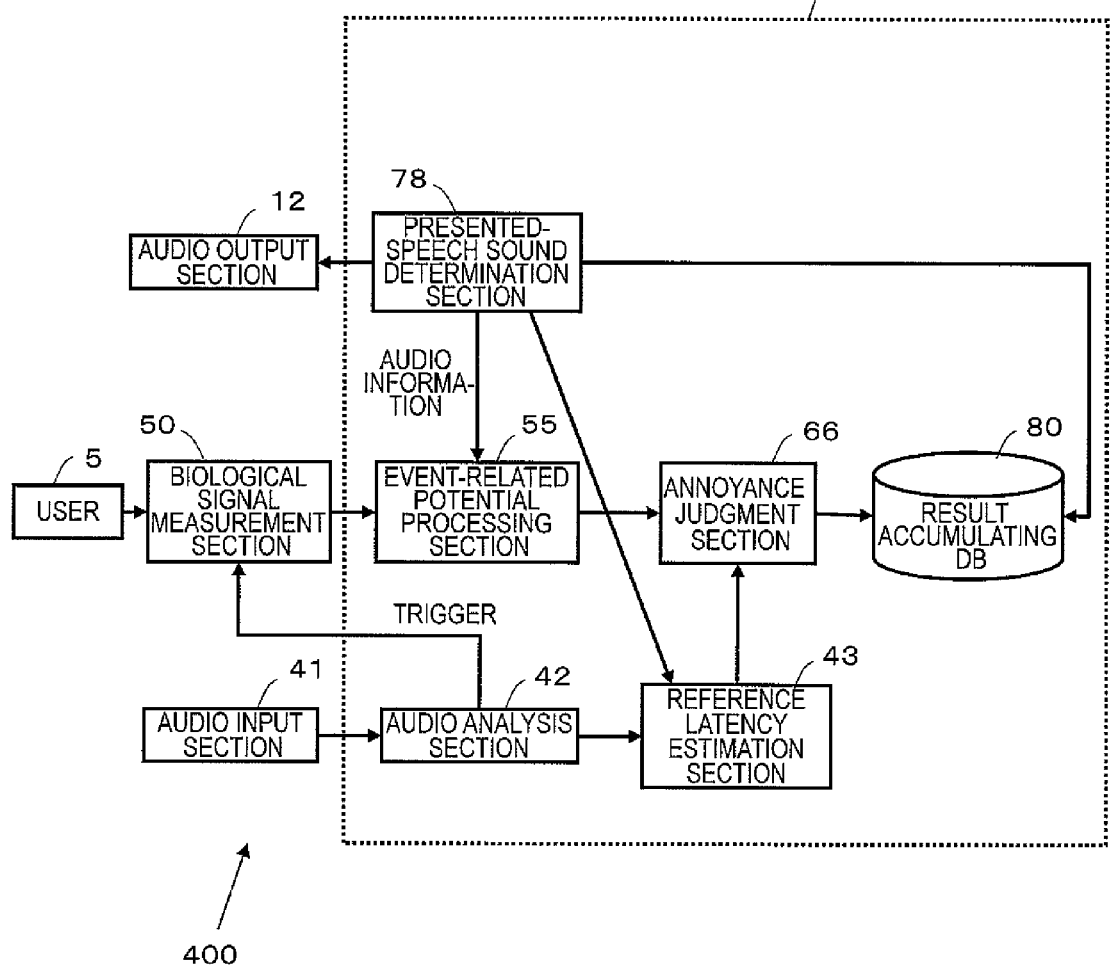
FIG. 26 is a diagram showing the functional block construction of an annoyance judgment system 400 for speech sound listening according to Embodiment 4.

FIG. 26 shows the functional block construction of an annoyance judgment system 400 for speech sound listening of the present embodiment. The annoyance judgment system 400 for speech sound listening includes a character output section 12, an audio input section 41, a biological signal measurement section 50, and an annoyance judgment apparatus 4 for speech sound listening. Any block which has an identical counterpart in FIG. 15 is denoted by a like reference numeral, and the description thereof is omitted.

The annoyance judgment system 400 for speech sound listening of the present embodiment differs from the annoyance judgment system 100 for speech sound listening of Embodiment 1 in that the audio input section 41 is additionally introduced, and that the character output section 12 is provided instead of the audio output section 11. Due to the addition of these component elements, the annoyance judgment apparatus 4 for speech sound listening has different functionality than that of the annoyance judgment apparatus 1 for speech sound listening.

The character output section 12 is a display device which outputs text information of a speech sound to speaker A, e.g., a liquid crystal display. As the text information, monosyllabic speech sounds to be uttered by speaker A (e.g., "あ (a)", "だ (da)", "し (shi)") are presented. In addition to the monosyllabic speech sounds, information of a sound pressure concerning how loud speaker A is supposed to make utterances may be indicated. Information concerning sound pressure may be "in a usual speaking voice", "in a loud voice", or "in a soft voice", for example.

The audio input section 41 is a microphone with which to collect the audios as uttered by speaker A.

The annoyance judgment apparatus 4 for speech sound listening will be described later.

Figure 27:
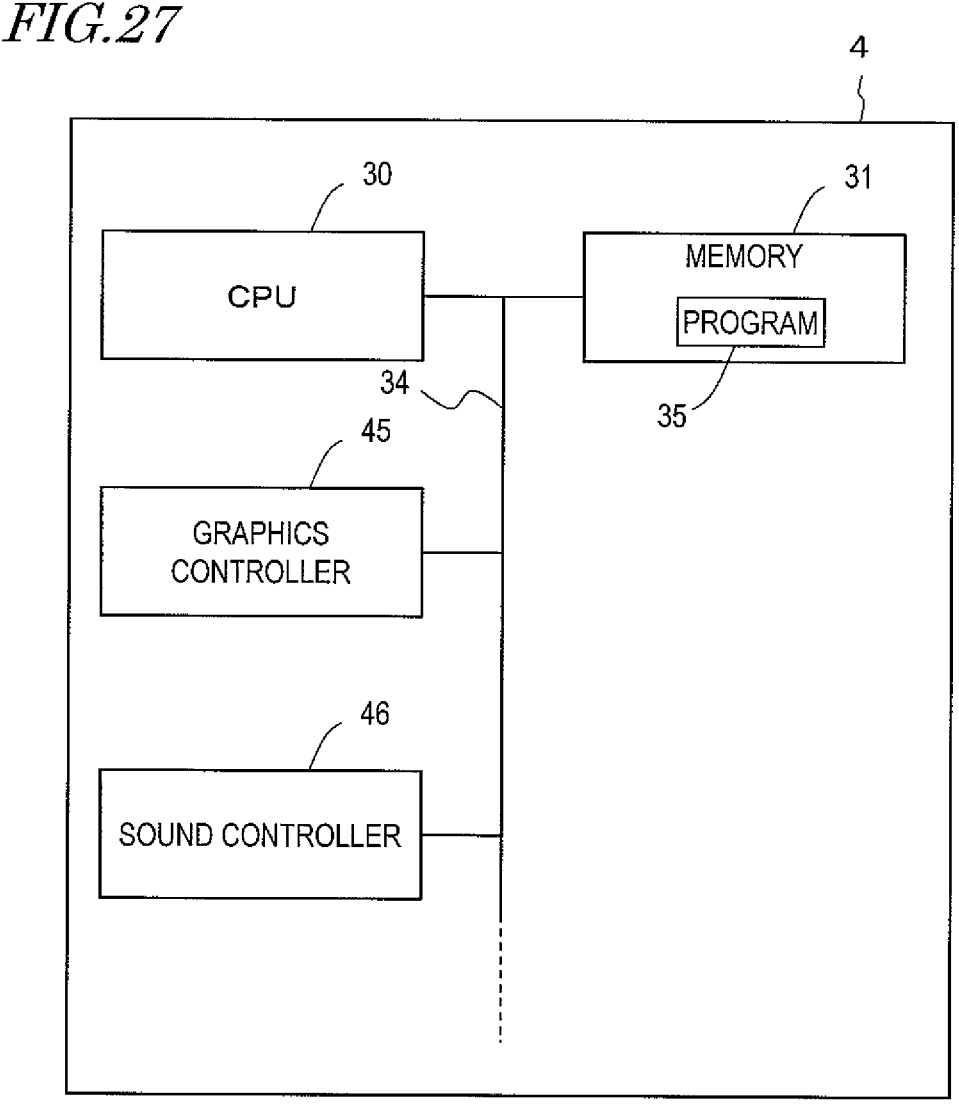
FIG. 27 is a diagram showing the hardware construction of an annoyance judgment apparatus 4 for speech sound listening according to Embodiment 4.

FIG. 27 shows the hardware construction of the annoyance judgment apparatus 4 for speech sound listening. Any constituent element which has an identical counterpart in Embodiment 1 as shown in FIG. 14 is denoted by a like reference numeral, and the description thereof is omitted. Differences from FIG. 14 are that: a sound controller 46 is additionally introduced; a graphics controller 45 is provided instead of the audio controller 32; and the speech sound DB 71 is omitted from the memory 31.

The sound controller 46 subjects an audio waveform which has been uttered by speaker A and input via the audio input section 41 to an A/D conversion, and sends the resultant digital audio data to the CPU 30.

In accordance with an instruction from the CPU 30, the graphics controller 45 outputs text information of the speech sound for presentation to the character output section 12.

The processes by the annoyance judgment apparatus 4 for speech sound listening of the present embodiment, e.g., analysis of the audio waveform, are realized as a program which defines a different process from that of the program 35 described in Embodiment 1 (FIG. 14) is executed.

FIG. 26 is referred to again. One large difference of the annoyance judgment apparatus 4 for speech sound listening of the present embodiment from the annoyance judgment apparatus 1 for speech sound listening of Embodiment 1 is that an audio analysis section 42 and a reference latency estimation section 43 are additionally introduced. Moreover, in the present embodiment, the presented-speech sound determination section 78 and the annoyance judgment section 66 determine a speech sound type to be uttered by speaker A, determines a reference N1 component latency for the speech sound audio uttered by speaker A, and performs an annoyance judgment based on that reference latency.

Hereinafter, the presented-speech sound determination section 78, the audio analysis section 42, the reference latency estimation section 43, and the annoyance judgment section 66 will be described.

The presented-speech sound determination section 78 refers to a previously provided speech sound list which is retained therein to randomly determine a speech sound to be uttered by speaker A, and outputs it to speaker A via the character output section 12. Then, the presented-speech sound determination section 78 sends the information of the determined speech sound to the event-related potential processing section 55 and the reference latency estimation section 43. The speech sound list may be the 20 speech sounds of the 67S list, or the 50 sounds of the 57S list, for example.

From the sound information having been input to the audio input section 41, the audio analysis section 42 detects the timing with which speaker A uttered the audio, and analyzes characteristic features concerning the audio, e.g., the consonant duration, the consonant intensity, the vowel intensity. Then, at the timing of detecting the utterance of speaker A, the audio analysis section 42 sends a trigger to the biological signal measurement section 50. Furthermore, the audio analysis section 42 sends information concerning the audio characteristic features to the reference latency estimation section 42.

Based on the information concerning the audio characteristic features received from the audio analysis section 42 and the speech sound information received from the presented-speech sound determination section 78, the reference latency estimation section 43 estimates a reference N1 component latency for that speech sound.

Similarly to the annoyance judgment section 65 of Embodiment 1, based on the latency of an N1 component in the electroencephalogram data received from the event-related potential processing section 55, the annoyance judgment section 66 judges whether the user felt annoyed or not. For example, the annoyance judgment section 66 compares the peak latency of a negative potential at a latency from 50 ms to 350 ms against the reference latency (threshold value) which has been estimated by the reference latency estimation section 43. Then, if the peak latency of the N1 component is shorter than the threshold value, an "annoying" judgment is made; and if the peak latency is longer than the predetermined threshold value, a "not annoying" judgment is made.

Next, with reference to the flowchart of FIG. 28, an overall procedure of processing performed by the annoyance judgment system 400 for speech sound listening will be described.

FIG. 28 shows a processing procedure by the speech sound intelligibility system 400 of the present embodiment. In FIG. 28, any step where a process identical to a process (FIG. 19) by the annoyance judgment system 100 for speech sound listening will be denoted by a reference numeral, and the description thereof will be omitted.

The processes by the annoyance judgment system 400 for speech sound listening of the present embodiment differ from the processes by the annoyance judgment system 100 for speech sound listening of Embodiment 1 in steps S401 to S407. Any other steps have already been described in connection with FIG. 19, and the descriptions thereof are omitted.

At step S401, referring to the speech sound list retained in the presented-speech sound determination section 78, the presented-speech sound determination section 78 randomly determines a speech sound type to be uttered by speaker A, and outputs the determined speech sound to speaker A via the character output section 12.

At step S402, from the sound information having been input to the audio input section 41, the audio analysis section 42 detects the timing with which speaker A uttered the audio, and at the timing of detection, sends a trigger to the biological signal measurement section 50.

At step S403, the audio analysis section 42 analyzes the characteristic features of the audio detected from the sound information input to the audio input section 41, e.g., the consonant duration, the consonant intensity, and the vowel intensity. Then, the audio analysis section 42 sends the analysis results to the reference latency estimation section 43.

At step S404, based on the information concerning the audio characteristic features received from the audio analysis section 42 and the speech sound information received from the presented-speech sound determination section 78, the reference latency estimation section 43 estimates a reference N1 component latency for that speech sound. The reference latency is estimated by adding a predetermined positive value, which is based on the consonant duration or consonant intensity of the audio, to a predetermined base latency. The predetermined base latency may be the latency of an average N1 component of a generic user when hearing a vowel at 90 dB SPL, for example. Specifically, it may be 100 ms. Moreover, the predetermined positive value is determined for each consonant. For example, in the case of a speech sound whose consonant portion has a weak intensity, the consonant duration having been analyzed by the audio analysis section 42 may be regarded as the predetermined positive value. In the case of a speech sound whose consonant portion has a strong intensity, the intensity of the consonant portion having been analyzed by the audio analysis section 42 or the time which elapses until the intensity of a specific frequency in the consonant portion becomes equal to or greater than a predetermined value may be used as the predetermined positive value. The relative strength of the consonant intensity may be determined based on the speech sound information received from the presented-speech sound determination section 78. Then, the estimated reference latency is sent to the annoyance judgment section 66.

At step S405, the event-related potential processing section 55 sends the actual audio to be presented that has been received from the presented-speech sound determination section 70 and the event-related potential that has been received from the biological signal measurement section 50 to the annoyance judgment section 66.

At step S406, based on the latency of an N1 component in the electroencephalogram data received from the event-related potential processing section 55, the annoyance judgment section 66 judges whether the user felt annoyed or not. For example, the annoyance judgment section 65 compares the peak latency of a negative potential at a latency from 50 ms to 350 ms against the reference latency received from the reference latency estimation section 43. Then, if the peak latency of the N1 component is shorter than the reference latency, an "annoying" judgment is made; and if the peak latency is longer than the reference latency, a "not annoying" judgment is made.

At step S407, the result accumulating DB 80 receives the speech sound type from the presented-speech sound determination section 77, and receives information of the annoyance judgment result from the annoyance judgment section 66. Then, accumulates the information of the annoyance judgment result for each speech sound, for example.

Through such processes, the characteristic features of an audio which has been uttered by speaker A are analyzed; a reference N1 component latency is estimated for each audio characteristic feature; and a comparison between the latency of an N1 component of the measured electroencephalogram data and the estimated reference N1 component latency can be made. In the case where speaker A is allowed to freely utter monosyllabic speech sounds, while the audio analysis section 42 recognizes the audios, the presented-speech sound determination section 78 and the character output section 12 may be omitted.

In accordance with the annoyance judgment system 400 for speech sound listening of the present embodiment, annoyance judgment in speech sound listening can be realized in real time by using audios uttered by speaker A. As a result, an acoustic aiding process which does not induce annoyance and aural fatigue in the user can be realized, without much trouble being incurred by speaker A and a hearing aid fitting expert.

Moreover, in the present embodiment, instead of sending a trigger to the biological signal measurement section 50, the audio analysis section 42 may send a trigger to the event-related potential processing section 55. In this case, the biological signal measurement section 50 may constantly measure an electroencephalogram, cut out an event-related potential as needed by the event-related potential processing section 55, and subject it to a baseline correction.

In the above-described embodiments, the annoyance judgment section is illustrated as performing an operation of "judging", and the presented-speech sound determination section as performing an operation of "determining", for example. However, these expressions are employed for facilitating human understanding of the respective operations, and it is not intended that the apparatus actually has the discretion in "judging" and "determining" what is to be externally output. The "annoyance judgment section" or the "presented-speech sound determination section", as a component element of the apparatus, may simply perform a certain process when certain conditions are met.

For example, when the N1 component latency of the electroencephalogram data is shorter than a reference latency, the annoyance judgment section may accumulate this result under the classification that the user felt annoyed, or when the N1 component latency of the electroencephalogram data is longer than the reference latency, the annoyance judgment section may accumulate this result under the classification that the user has not felt annoyed. On the other hand, the presented-speech sound determination section may cause speech sounds to be selected in random order by referring to the speech sound DB, and a sound pressure to be randomly selected for output at the audio output section. Such processes are conveniently described by using the expressions "judge" and "determine".

The above explanation also applies when the process according to the present disclosure is executed as a method.

With the annoyance judgment apparatus for speech sound listening according to the present disclosure and an annoyance judgment system for speech sound listening which incorporates the annoyance judgment apparatus for speech sound listening, in addition to the intelligibility as to whether a speech sound has been aurally distinguished or not, a quantitative annoyance judgment in speech sound listening can be made based on an electroencephalogram when listening to the speech sound. As a result, an acoustic aiding process which does not induce annoyance and aural fatigue in the user can be selected. Thus, the technique disclosed herein is applicable to the fitting for any and all hearing aid users.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. An annoyance judgment system comprising:
   one or more memories storing a speech sound database retaining a plurality of monosyllabic speech sounds such that, for each speech sound, the speech sound and a reference latency of an electroencephalogram negative component corresponding to the speech sound are retained in association; and
   circuitry which in operation is configured to:
   measure an electroencephalogram signal of a user;
   determine a monosyllabic speech sound to be presented by referring to the speech sound database;
   present the determined speech sound to the user;
   judge annoyance of the output speech sound by comparing a peak latency of a negative component of the measured electroencephalogram signal in a range from 50 ms to 350 ms from a starting point, the starting point being a point in time at which the speech sound is presented, against the reference latency corresponding to the determined speech sound that is retained in the speech sound database; and
   output gain settings for presenting speech sounds based on the annoyance judgment.

2. The annoyance judgment system of claim 1, wherein the speech sound database keeps the association between each speech sound and a reference latency of an electroencephalogram negative component corresponding to the speech sound on the basis of a duration or intensity of a consonant contained in the speech sound.

3. The annoyance judgment system of claim 1, wherein, if the peak latency of the negative component is equal to or smaller than the reference latency, the circuitry is configured to judge that the audio signal is annoying to the user, and if the peak latency of the negative component is greater than the reference latency, the circuitry judges that the audio signal is not annoying to the user.

4. The annoyance judgment system of claim 1, wherein the circuitry further is configured to:
   take a summation of event-related potentials of the electroencephalogram signal according to a predetermined criterion and configured to output a result of the summation,
   determine two or more speech sounds;
   present the determined speech sounds; and
   among the determined speech sounds, take a summation of event-related potentials in response to speech sounds of a same speech sound type or a same sound pressure, each event-related potential being based on a point in time of presenting the respective speech sound as a starting point.

5. The annoyance judgment system of claim 1, wherein, as the peak latency, the circuitry is configured to adopt: a point in time at which a negative component of the electroencephalogram signal in a range from 50 ms to 350 ms from a starting point takes a smallest potential, the starting point being a point in time at which the determined speech sound is presented; or a peak latency that is associated with a template having a highest degree of matching, among previously-provided templates of N1 component waveforms, with the electroencephalogram signal.

6. The annoyance judgment system of claim 5, wherein the circuitry is configured to take a summation of event-related potentials with respect to a consonant, or with respect to a group of speech sounds whose differences in reference latency is smaller than a predetermined value.

7. The annoyance judgment system of claim 1, wherein the one or more memories further stores a result accumulating database configured to accumulate information indicating a result of annoyance judgment for the speech sound, wherein the result accumulating database accumulates information indicating the result of annoyance judgment for the speech sound with respect to a consonant, or a group of speech sounds whose differences in reference latency is smaller than a predetermined value.

8. The annoyance judgment system of claim 1, wherein the circuitry further is configured to select a type of acoustic aiding process for the presented speech sound, and is configured to modify data of the speech sounds retained in the speech sound database based on the selected acoustic aiding process.

9. The annoyance judgment system of claim 1, wherein the circuitry further is configured to switch between a calibration mode of determining reference latencies of negative components for the user and an assessment mode of assessing annoyance, wherein, in the calibration mode, the circuitry is configured to select a vowel, and calculates a reference latency for each speech sound based on a latency of the negative component for the vowel; and after switching to the assessment mode, the circuitry is configured to compare the peak latency of the negative component against the calculated reference latency.

10. The annoyance judgment system of claim 9, wherein, in the calibration mode, when a vowel is selected, the circuitry sets a latency of an N1 component for the vowel as a reference latency for the vowel, and calculates a reference latency for each consonant by adding a positive value which is adapted to a duration or intensity of a consonant portion to the reference latency for the vowel.

11. An annoyance judgment apparatus comprising circuitry which in operation is configured to:

determine a monosyllabic speech sound to be presented by referring to a speech sound database retaining a plurality of monosyllabic speech sounds such that, for each speech sound, the speech sound and a reference latency of an electroencephalogram negative component corresponding to the speech sound are retained in association;

in an electroencephalogram signal of a user measured by a biological signal measurement circuitry, compare a peak latency of a negative component of the electroencephalogram signal in a range from 50 ms to 350 ms from a starting point, the starting point being a point in time at which the speech sound is presented to the user, against the reference latency corresponding to the determined speech sound that is retained in the speech sound database, and outputting a difference between the peak latency and the reference latency; and adjust the speech sound based on the difference output from the circuitry.

12. An annoyance judgment method comprising the steps of:

operating circuitry to perform the steps of:
measuring an electroencephalogram signal of a user;
determining a monosyllabic speech sound to be presented by referring to a speech sound database retaining a plurality of monosyllabic speech sounds such that, for each speech sound, the speech sound and a reference latency of an electroencephalogram negative component corresponding to the speech sound are retained in association;
presenting the determined speech sound to the user;
judging annoyance of the output speech sound by comparing a peak latency of a negative component of the measured electroencephalogram signal in a range from 50 ms to 350 ms from a starting point, the starting point being a point in time at which the speech sound is presented, against the reference latency corresponding to the determined speech sound that is retained in the speech sound database; and
outputting gain settings for presenting speech sounds based on the annoyance judgment.

13. A non-transitory computer-readable medium storing a computer program, to be executed by a computer mounted in an annoyance judgment system for speech sound listening, wherein the computer program causes the computer in the annoyance judgment system to execute the steps of:

receiving an electroencephalogram signal of a user;
determining a monosyllabic speech sound to be presented by referring to a speech sound database retaining a plurality of monosyllabic speech sounds such that, for each speech sound, the speech sound and a reference latency of an electroencephalogram negative component corresponding to the speech sound are retained in association;
presenting the determined speech sound to the user;
judging annoyance of the output speech sound by comparing a peak latency of a negative component of the measured electroencephalogram signal in a range from 50 ms to 350 ms from a starting point, the starting point being a point in time at which the speech sound is presented, against the reference latency corresponding to the determined speech sound that is retained in the speech sound database; and
outputting gain settings for presenting speech sounds based on the annoyance judgment.

14. An annoyance judgment system comprising circuitry which in operation is configured to:

measure an electroencephalogram signal of a user;
input an audio signal of an utterance by a specified speaker;
output a trigger upon detecting a timing at which the audio signal is input, and analyzing a characteristic feature of the audio concerning a duration and an intensity of a consonant portion;
based on the characteristic feature analyzed, estimate a reference latency of an electroencephalogram negative component;
judge annoyance by comparing a peak latency of a negative component of the measured electroencephalogram signal in a range from 50 ms to 350 ms from the trigger as a starting point against the reference latency estimated by the circuitry; and
output gain settings for presenting speech sounds based on the annoyance judgment.

15. The annoyance judgment system of claim 14, wherein the circuitry is configured to output text information indicating a speech sound for the specified speaker to utter, wherein an audio signal of an utterance by the specified speaker is input to the audio input section based on the text information having been output by the circuitry.

16. The annoyance judgment system of claim 15, wherein, the circuitry further outputs information concerning a sound pressure indicating a loudness with which the specified speaker is to utter the monosyllabic speech sound; and an audio signal of an utterance by the specified speaker is input to the audio input section based on the text information and information concerning sound pressure having been output by the circuitry.

17. The annoyance judgment system of claim 15, wherein the circuitry is configured to determine a speech sound for the specified speaker to utter by referring to a previously-provided speech sound list, wherein the circuitry outputs text information indicating the determined speech sound.

18. The annoyance judgment system of claim 17, wherein circuitry estimates the reference latency of an electroencephalogram negative component based on the characteristic feature analyzed by the circuitry and on the speech sound for the specified speaker to utter that is determined by the circuitry.

19. The annoyance judgment system of claim 17, wherein the circuitry estimates the reference latency of an electroencephalogram negative component by adding a predetermined positive value to a previously-provided base latency, the predetermined positive value being adapted to a consonant duration or consonant intensity of the audio.

20. An annoyance judgment method comprising the steps of:
    operating circuitry to perform the steps of:
    measuring an electroencephalogram signal of a user;
    inputting an audio signal of an utterance by a specified speaker;
    outputting a trigger upon detecting a timing at which the audio signal is input, and analyzing a characteristic feature of the audio concerning a duration and an intensity of a consonant portion;
    estimating a reference latency of an electroencephalogram negative component, based on the characteristic feature analyzed by the analyzing step;
    judging annoyance by comparing a peak latency of a negative component of the measured electroencephalogram signal in a range from 50 ms to 350 ms from the trigger as a starting point against the reference latency estimated by the estimating step; and
    outputting gain settings for presenting speech sounds based on the annoyance judgment.

* * * * *